United States Patent [19]

Chucholowski et al.

[11] Patent Number: 4,906,624
[45] Date of Patent: Mar. 6, 1990

[54] 6-(((SUBSTITUTED)PYRIDIN-3-YL)ALKYL)- AND ALKENYL)-TETRAHYDRO-4-HYDROXYPYRAN-2-ONE INHIBITORS OF CHOLESTEROL BIOSYNTHESIS

[75] Inventors: Alexander W. Chucholowski, Ypsilanti; Mark W. Creswell, Chelsea; Bruce D. Roth, Ann Arbor; Drago R. Sliskovic, Ypsilanti, all of Mich.

[73] Assignee: Warner-Lambert Company, Morris Plains, N.J.

[21] Appl. No.: 226,190

[22] Filed: Aug. 2, 1988

Related U.S. Application Data

[63] Continuation-in-part of Ser. No. 94,198, Sep. 8, 1987, abandoned.

[51] Int. Cl.$^4$ .................. C07D 405/06; A61K 31/365
[52] U.S. Cl. ..................................... 514/210; 514/212; 514/235.5; 514/252; 514/256; 514/318; 514/332; 514/333; 514/336; 514/343; 540/481; 540/597; 544/82; 544/131; 544/295; 544/296; 544/333; 544/357; 544/360; 546/187; 546/193; 546/256; 546/268; 546/281; 546/284

[58] Field of Search ............... 546/268, 256, 284, 276, 546/275, 193, 187, 281; 544/333, 360, 82, 131, 295, 296, 357; 514/256, 333, 332, 336, 235.5, 210, 318, 212, 252, 343; 540/597, 461

[56] References Cited

U.S. PATENT DOCUMENTS

| 4,375,475 | 3/1983 | Willard et al. ...................... 514/460 |
| 4,613,610 | 9/1986 | Wareing .............................. 514/406 |
| 4,647,576 | 3/1987 | Hoefle et al. ........................ 514/422 |
| 4,681,893 | 7/1987 | Roth ................................... 514/422 |
| 4,735,958 | 4/1988 | Roth et al. .......................... 514/343 |

FOREIGN PATENT DOCUMENTS

| WO86/00307 | 7/1986 | PCT Int'l Appl. ................. 514/406 |
| WO86/28274 | 7/1986 | PCT Int'l Appl. ................. 514/406 |
| 2110682 | 6/1983 | United Kingdom ............... 546/268 |

Primary Examiner—Mary C. Lee
Assistant Examiner—Zinna Northington Davis
Attorney, Agent, or Firm—Elizabeth M. Anderson

[57] ABSTRACT

Certain trans-6-[[(substituted)pyridin-3-yl]-alkyl- and alkenyl]tetrahydro-4-hydroxypyran-2-ones and the corresponding ring-opened acids derived therefrom are potent inhibitors of the enzyme 3-hydroxy-3-methylglutaryl-coenzyme A reductase (HMG-CoA reductase) and are useful as hypocholesterolemic and hypolipidemic agents.

12 Claims, No Drawings

6-(((SUBSTITUTED)PYRIDIN-3-YL)ALKYL)- AND ALKENYL)-TETRAHYDRO-4-HYDROXYPYRAN-2-ONE INHIBITORS OF CHOLESTEROL BIOSYNTHESIS

CROSS-REFERENCE TO RELATED APPLICATION

This application is a continuation-in-part of copending application U.S. Ser. No. 094,198, now abandoned, filed Sept. 8, 1987.

BACKGROUND OF THE INVENTION

The present invention is related to compounds and pharmaceutical compositions useful as hypocholesterolemic and hypolipidemic agents. More particularly, this invention concerns certain trans-6-[[(substituted)pyridin-3-yl]-alkyl- and alkenyl]tetrahydro-4-hydroxypyran-2-ones and the corresponding ring-opened acids derived therefrom which are potent inhibitors of the enzyme 3-hydroxy-3-methylglutaryl-coenzyme A reductase (HMG-CoA reductase), pharmaceutical compositions containing such compounds, and a method of lowering blood serum cholesterol levels employing such pharmaceutical compositions.

High levels of blood cholesterol and blood lipids are conditions which are involved in the onset of arteriosclerosis. It is well known that inhibitors of HMG-CoA reductase are effective in lowering the level of blood plasma cholesterol, especially low density lipoprotein cholesterol (LDL-C), in man (cf. M. S. Brown and J. L. Goldstein, *New England Journal of Medicine* (1981), 305, No. 9, 515–517). It has now been established that lowering LDL-C levels affords protection from coronary heart disease (cf. *Journal of the American Medical Association* (1984) 251, No. 3, 351–374).

Moreover, it is known that certain derivatives of mevalonic acid (3,5-dihydroxy-3-methylpentanoic acid) and the corresponding ring-closed lactone form, mevalonolactone, inhibit the biosynthesis of cholesterol (cf. F. M. Singer, et al, *Proc. Soc. Exper. Biol. Med.* (1959), 102, 270) and F. H. Hulcher, *Arch. Biochem. Biophys.* 30 (1971), 146, 422.

U.S. Pat. Nos. 3,983,140; 4,049,495 and 4,137,322 disclose the fermentative production of a natural product, now called compactin, having an inhibitory effect on cholesterol biosynthesis. Compactin has been shown to have a complex structure which includes a mevalonolactone moiety (Brown, et al, *J. Chem. Soc. Perkin I*, (1976), 1165).

U.S. Pat. No. 4,255,444 to Oka, et al, discloses several synthetic derivatives of mevalonolactone having antilipidemic activity.

U.S. Pat. Nos. 4,198,425 and 4,262,013 to Mitsue, et al, disclose aralkyl derivatives of mevalonolactone which are useful in the treatment of hyperlipidemia.

U.S. Pat. No. 4,375,475 to Willard, et al, discloses certain substituted 4-hydroxytetrahydropyran-2-ones which, in the 4(R)-trans stereoisomeric form, are inhibitors of cholesterol biosynthesis.

U.S. Pat. No. 4,647,576 to Hoefle, et al, discloses certain trans-6-[2-[(substituted)-pyrrol-1-yl]alkyl]tetrahydro-4-hydroxypyran-2-ones and the corresponding lactone ring-opened acids as inhibitors of cholesterol biosynthesis.

U.S. Pat. No. 4,681,893 to Roth discloses certain trans-6-[[(2-, (3-, or (4-carboxamido-substituted)pyrrol-1-yl]alkyl- or alkenyl]-tetrahydro-4-hydroxypyran-2-one inhibitors of cholesterol biosynthesis.

SUMMARY OF THE INVENTION

In accordance with the present invention, there are provided certain trans-6-[[2-(substituted)pyridin-3-yl]alkyl- or alkenyl]tetra-hydro-4-hydroxypyran-2-ones and the corresponding ring-opened hydroxy-acids derived therefrom which are potent inhibitors of cholesterol biosynthesis by virtue of their ability to inhibit the enzyme 3-hydroxy-3-methylglutaryl coenzyme A reductase (HMG-CoA reductase).

In particular, in its broadest chemical compound aspect, the present invention provides compounds of structural Formula I

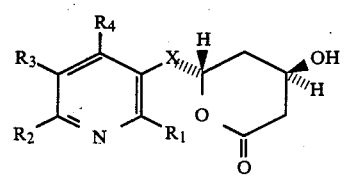

and the N-oxide thereof wherein X is —CH2CH2— or —CH=CH— (preferably in the (E) trans configuration).

$R_1$ and $R_4$ are independently alkyl of from one to six carbons; trifluoromethyl; cyclopropyl; cyclohexyl; cyclohexylmethyl; phenyl; phenyl substituted with fluorine, chlorine, bromine; hydroxy, trifluoromethyl, alkyl of from one to four carbon atoms, or alkoxy of from one to four carbon atoms; phenylmethyl; phenylmethyl substituted with fluorine, chlorine, bromine; hydroxy, trifluoromethyl, alkyl of from one to four carbon atoms, or alkoxy of from one to four carbon atoms; 2-, 3-, or 4-pyridinyl; 2-, 3-, or 4-pyridinyl-N-oxide; 2-, 4-, or 5-pyrimidinyl; or 2-, 3-thienyl; CH2OH; chlorine; bromine; or NR'R'' wherein R' and R'' are each independently hydrogen, alkyl, or together with the nitrogen to which they are attached form

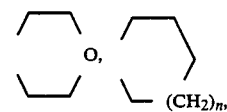

wherein n' is an integer of from 0 to 5;

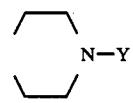

wherein Y is hydrogen or an alkyl of from one to four carbon atoms.

$R_1$ is also CN; OR; S(O)$_n$R wherein n is 0, 1, or 2, and R is lower alkyl, phenyl, substituted phenyl, benzyl or substituted benzyl;

$R_2$ is selected from hydrogen; alkyl of from one to six carbon atoms; trifluoromethyl; cyclopropyl; phenyl; phenyl substituted with fluorine, chlorine, bromine; hydroxy, trifluoromethyl, alkyl of from one to four carbon atoms, or alkoxy of from one to four carbon atoms; 2-, 3-, or 4-pyridinyl; 2-pyridinyl-N-oxide; 2-, 4-, or 5-pyrimidinyl; or 2-, or 3-thienyl, CH₂OH, chlorine, bromine or NR'R" as defined above.

R₃ is selected from hydrogen; alkyl of from one to six carbon atoms; cyano; CH₂NH₂; nitro; —NR₅R₆ where R₅ and R₆ are independently hydrogen or alkyl of from one to four carbon atoms; phenyl; —NHCOR₇ where R₇ is alkyl of from one to four carbon atoms; —COR₈ where R₈ is hydroxyl, alkoxy of from one to six carbon atoms, phenoxy, —NR₅R₆, where R₅ and R₆ are as defined above, vinyl, alkoxy from one to four carbon atoms, hydroxy or CH₂OH.

Also contemplated as falling within this aspect of the invention are the corresponding dihydroxy-acid compounds of Formula II corresponding to the opened form of the lactone ring of compounds of Formula I

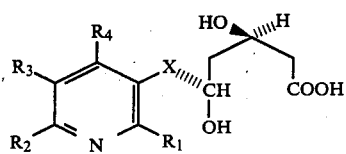

and the N-oxide thereof where X, R₁, R₂, R₃, and R₄ are as defined above, and the pharmaceutically acceptable salts thereof, all of the compounds being in the trans racemate of the tetrahydropyran moiety.

In another aspect of the present invention, there is provided a method of preparing compounds of Formula I above by (a) first reacting a substituted [(pyridin-3-yl)alkyl- or alkenyl] aldehyde compound of Formula III

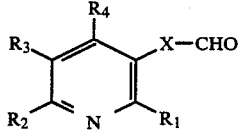

where X, R₁, R₂, R₃, and R₄ are as defined above, with the alkali metal salt of the dianion of methyl acetoacetate to form a compound of structural Formula IV

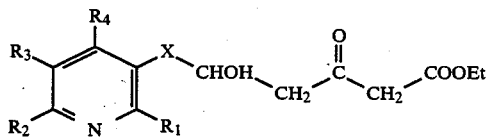

where X, R₁, R₂, R₃, and R₄ are as defined above, then successively (b) reducing compound IV with a trialkylborane and sodium borohydride and (c) oxidizing with alkaline hydrogen peroxide to produce an ester compound of Formula V

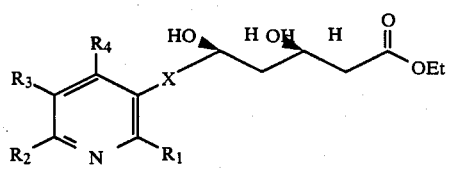

and finally (d) hydrolyzing and cyclizing, if desired, the ester compound of Formula V to a lactone compound of Formula I by heating in an inert solvent or, alternatively converting, if desired, the acid to a pharmaceutically acceptable salt.

In another aspect, the present invention provides pharmaceutical compositions, useful as hypolipidemic or hypocholesterolemic agents, comprising a hypolipidemic or hypocholesterolemic effective amount of a compound in accordance with this invention as set forth above in combination with a pharmaceutically acceptable carrier.

In another aspect, the present invention provides a method of inhibiting cholesterol biosynthesis in a patient in need of such treatment by administering a pharmaceutical composition in accordance with the present invention as defined above.

DETAILED DESCRIPTION

In a first preferred subgeneric chemical compound aspect, the present invention provides compounds of Formula I above wherein X is —CH2CH2—, and R₁, R₂, R₃, and R₄ are as defined above and the configuration in the lactone ring is R*R*.

In a second preferred subgeneric chemical compound aspect, the present invention provides compounds of Formula I above where X is —CH=CH—, most preferably in the (E)-trans form and the configuration in the lactone ring is R*S*.

As used throughout this specification and the appended claims, the term "alkyl" denotes a branched or unbranched saturated hydrocarbon group derived by the removal of one hydrogen atom from an alkane. The term "lower alkyl" denotes alkyl of from one to four carbon atoms.

The term "alkoxy" denotes an alkyl group, as just defined, attached to the parent molecular residue through an oxygen atom.

Specific examples of compounds contemplated as falling within the scope of the present invention include the following:

trans-tetrahydro-4-hydroxy-6-[2-(2-methyl-4-phenyl-3-pyridinyl)ethyl]-2H-pyran-2-one.

[4α,6β(E)]-tetrahydro-4-hydroxy-6-[2-(2-methyl-4-phenyl-3-pyridinyl)ethenyl]-2H-pyran-2-one.

[4α,6β(E)]-6-[2-(2,6-dimethyl-4-phenyl-3-pyridinyl)ethenyl]tetrahydro-4-hydroxy-2H-pyran-2-one.

[4α,6β(E)]-6-[2-[4-(4-fluorophenyl)-2,6-dimethyl-3-pyridinyl]ethenyl]tetrahydro-4-hydroxy-2H-pyran-2-one.

[2α,4β(E)]-4-(4-fluorophenyl)-2,6-dimethyl-5-[2-(tetrahydro-4-hydroxy-6-oxo-2H-pyran-2-yl)ethenyl]-3-pyridinecarbonitrile.

[R*,R*]-β,δ-dihydroxy-2-methyl-4-phenyl-3-pyridineheptanoic acid, or a lower alkyl ester or pharmaceutically acceptable salt thereof.

[R*,S*(E)]-3,5-dihydroxy-7-(2-methyl-4-phenyl-3-pyridinyl)-6-heptenoic acid, or a lower alkyl ester or pharmaceutically acceptable salt thereof.

[R*,S*(E)]-7-(2,6-dimethyl-4-phenyl-3-pyridinyl)-3,5-dihydroxy-6-heptenoic acid, or a lower alkyl ester or pharmaceutically acceptable salt thereof.

[R*,S*(E)]-7-[4-(4-fluorophenyl)-2,6-dimethyl-3-pyridinyl]-3,5-dihydroxy-6-heptenoic acid, or a lower alkyl ester or pharmaceutically acceptable salt thereof.

[R*,S*(E)]-7-[5-cyano-4-(4-fluorophenyl)-2,6-dimethyl-3-pyridinyl]-3,5-dihydroxy-6-heptenoic acid, or a lower alkyl ester or pharmaceutically acceptable salt thereof.

Preferred compounds of the present invention are:

[4α,6β(E)]-6-[2-(4-fluorophenyl)-2,6-bis(1-methylethyl)-3-pyridinyl]ethenyl]tetrahydro-4-hydroxy-2H-pyran-2-one;

[R*,S*(E)]-7-[4-(4-fluorophenyl)-2,6-bis(1-methylethyl)-3-pyridinyl]-3,5-dihydroxy-6-heptenoic acid, monosodium salt;

[4α,6β(E)]-6-[2-[4-(4-fluorophenyl)-6-methyl-2-(1-methylethyl)-3-pyridinyl]ethenyl]tetrahydro-4-hydroxy-2H-pyran-2-one;

[R*,S*-(E)]-7-[4-(4-fluorophenyl)-6-methyl-2-(1-methylethyl)-3-pyridinyl]-3,5-dihydroxy-6-heptenoic acid, monosodium salt;

[R*,S*-(E)]-7-[4-(4-fluorophenyl)-6-methyl-2-(1-methylethyl)-3-pyridinyl]-3,5-dihydroxy-6-heptenoic acid, hemicalcium salt;

[4α,6β(E)]-6-[2-[2,6-diethyl-4-(4-fluorophenyl)-3-pyridinyl]ethenyl]tetrahydro-4-hydroxy-2H-pyran-2-one;

[R*,S*-(E)]-7-[2,6-diethyl-4-(4-fluorophenyl)-3-pyridinyl]-3,5-dihydroxy-6-heptenoic acid, monosodium salt;

[4α,6β(E)]-6-[2-[4-(4-fluorophenyl)-5-methoxy-6-methyl-2-(1-methylethyl)-3-pyridinyl]ethenyl]tetrahydro-4-hydroxy-2H-pyran-2-one;

[R*,S*-(E)]-7-[4-(4-fluorophenyl)-5-methoxy-6-methyl-2-(1-methylethyl)-3-pyridinyl]-3,5-dihydroxy-6-heptenoic acid, monosodium salt;

[4α,6β(E)]-6-[2-[5-ethenyl-4-(4-fluorophenyl)-6-methyl-2-(1-methylethyl)-3-pyridinyl]ethenyl]tetrahydro-4-hydroxy-2H-pyran-2-one;

[R*,S*-(E)]-7-[5-ethenyl-4-(4-fluorophenyl)-6-methyl-2-(1-methylethyl)-3-pyridinyl]-3,5-dihydroxy-6-heptenoic acid, monosodium salt;

[4α,6β(E)]-6-[2-[4-(4-fluorophenyl)-6-methyl-2-(1-methylethyl)-3-pyridinyl]ethenyl]tetrahydro-4-hydroxy-2H-pyran-2-one, N-oxide;

[R*,S*-(E)]-7-(4-(4-fluorophenyl)-6-methyl-2-(1-methylethyl)-3-pyridinyl]-3,5-dihydroxy-6-heptenoic acid, N-oxide, monosodium salt.

Compounds of the present invention in which X is —CH=CH— are prepared by the general synthetic method outlined in Reaction Scheme 1. The preparation of compounds of the present invention where X is —CH$_2$CH$_2$— is outlined in Reaction Scheme 2.

Referring to Reaction Scheme 1, the 3-amino-acryl ester, represented by ethyl 3-amino-crotonate, 1, is condensed with a suitable enone, represented by trans-cinammaldehyde, 2, by heating the mixture in a suitable solvent such as ethanol in the presence of catalytic amounts of a base such as piperidine. (See Rapoport, et al. *J. Am. Chem. Soc.*, 98: 6650 (1976).

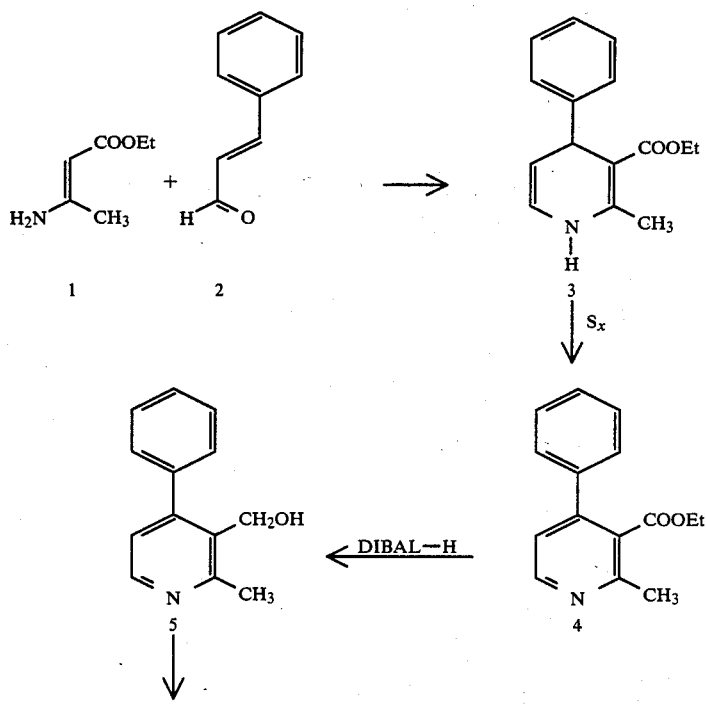

Reaction Scheme 1

-continued
Reaction Scheme 1
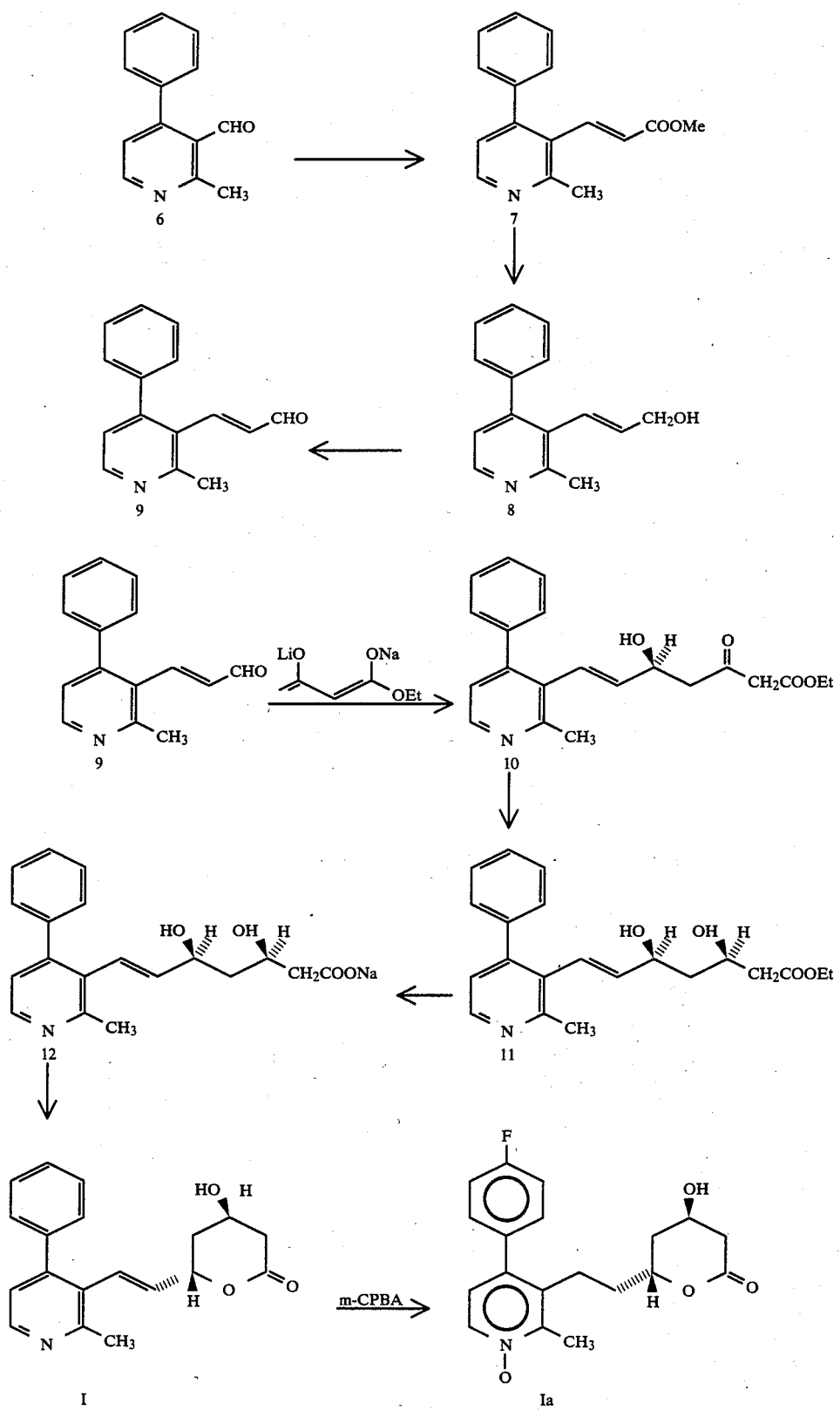
The resulting dihydropyridine, 3, is then aromatized by heating with a suitable dehydrating agent such as powdered sulfur at a temperature ranging between about 130° C. and 180° C.

The resulting pyridine, 4, is converted to the corresponding alcohol, 5, employing a suitable reducing agent such as lithium aluminum hydride or diisobutyl aluminum hydride in a polar aprotic solvent such as tetrahydrofuran under nitrogen at a low temperature.

The alcohol, 5, is then oxidized to the corresponding aldehyde by generally known methods. Using the method of Swern (Swern, et al, *J. Org. Chem.*, 43: 2480 (1978) where activated dimethylsulfoxide is the oxidant, yields the desired aldehyde, 6.

Wittig reaction of the aldehyde, 6, with an ylide such as carbomethoxy triphenylphosphorane in methylene chloride at room temperature produces the unsaturated trans-ester, 7, in high yield. The ester, 7, is reduced to the allyl alcohol, 8, using a well-known procedure employing two equivalents of diisobutyl aluminum hydride at −78° C.

The allyl alcohol, 8, is reoxidized to the aldehyde, 9, by Swern oxidation, followed by an aldol condensation to the sodium lithium dianion of ethyl acetoacetate at −78° C. in tetrahydrofuran. (See Kraus, et al, *J. Org. Chem.*, 48: 2111 (1983)) to form the 5-hydroxy-3-oxo-6-heptenoic acid-ethyl ester, 10.

The product of this condensation is then reduced in a sequence of steps in which it is first dissolved in a polar solvent such as tetrahydrofuran under a dry atmosphere. A small excess of triethylborane and catalytic amounts of 2,2-dimethylpropanoic acid are next added. The mixture is stirred at room temperature for a short period, after which it is cooled to a temperature preferably between −60° C. and −80° C. Dry methanol is added, followed by sodium borohydride. The mixture is kept at low temperature for 4–8 hours before treating it with hydrogen peroxide and ice water. The substituted 3,5-dihydroxy-6-heptenoic acid ethyl ester, 11, is isolated having the preferred R*,S* configuration.

The ester, 11, may be utilized as such in the pharmaceutical method of this invention, or may be converted, if desired, to the corresponding acid salt form such as the sodium salt, 12, employing basic hydrolysis by generally well-known methods. The free acid produced by neutralization of 12, can be dehydrated to the lactone, I, by heating in an inert solvent such as toluene with concomitant azeotropic removal of water and treatment with metachloroperbenzoic acid gives 1a.

Referring to Reaction Scheme 2, the unsaturated pyridine esters, 7, obtained by methods described in Reaction Scheme 1, are reduced by the action of hydrogen over Pd/C to produce the corresponding saturated pyridine ester compounds, 13. The saturated esters, 13, are reduced by the action of diisobutyl aluminum hydride to the corresponding alcohols, 14, which in turn are converted through the same reaction sequence shown in Reaction Scheme 1 to the compounds of this invention.

In the ring-opened dihydroxy acid form, compounds of the present invention react to form salts with pharmaceutically acceptable metal and amine cations formed from organic and inorganic bases.

The term "pharmaceutically acceptable metal cation" contemplates positively charged metal ions derived from sodium, potassium, calcium, magnesium, aluminum, iron, zinc and the like.

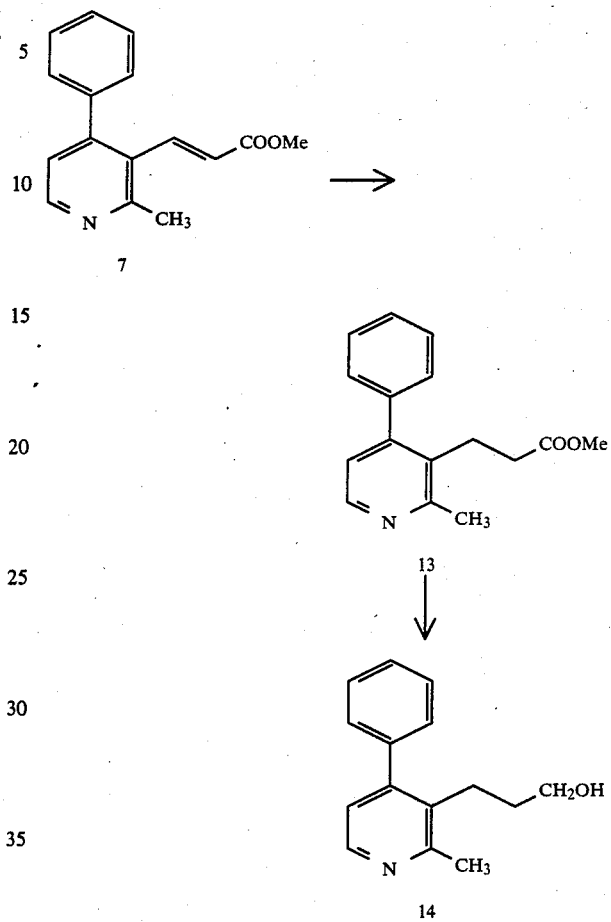

Reaction Scheme 2

The term "pharmaceutically acceptable amine cation" contemplates the positively charged ions derived from ammonia and organic nitrogenous bases strong enough to form such cations. Bases useful for the formation of pharmaceutically acceptable nontoxic base addition salts of compounds of the present invention form a class whose limits are readily understood by those skilled in the art. (See, for example, Berge, et al, "Pharmaceutical Salts," *J. Pharm. Sci.*, 66: 1–19 (1977)).

The free acid form of the compound may be regenerated from the salt, if desired, by contacting the salt with a dilute aqueous solution of an acid such as hydrochloric acid.

The base addition salts may differ from the free acid form of compounds of this invention in such physical characteristics as melting point and solubility in polar solvents, but are considered equivalent to the free acid forms for purposes of this invention.

The compounds of this invention can exist in unsolvated as well as solvated forms. In general, the solvated forms, with pharmaceutically acceptable solvents such as water, ethanol, and the like, are equivalent to the unsolvated forms for purposes of this invention.

The compounds of this invention are useful as hypocholesterolemic or hypolipidemic agents by virtue of their ability to inhibit the biosynthesis of cholesterol through inhibition of the enzyme 3-hydroxy-3-methyl-glutaryl-coenzyme A reductase (HMG-CoA reductase).

The ability of compounds of the present invention to inhibit the biosynthesis of cholesterol was measured by a method (designated CSI screen) which utilizes the procedure described by R. E. Dugan, et al, *Archiv. Biochem. Biophys.*, (1972), 152, 21–27. In this method, the level of HMG-CoA enzyme activity in standard laboratory rats is increased by feeding the rats a chow diet containing 5% cholestyramine for four days, after which the rats are sacrificed.

The rat livers are homogenized, and the incorporation of cholesterol-14C-acetate into nonsaponifiable lipid by the rat liver homogenate is measured. The micromolar concentration of compound required for 50% inhibition of sterol synthesis over a one-hour period is measured, and expressed as an $IC_{50}$ value.

The ability of compounds of the present invention to inhibit the biosynthesis of cholesterol was also measured by a method (designated AICS screen) which utilizes the procedure described by A. W. Alberts et al, *Proc. Natl. Acad. Sci.*, (1980), 77, pp 3957–3961.

In this method male Sprague-Dawley rats (200 g body weight) previously fed 5% cholestyramine for three days were randomly divided into groups (N=5/group) and given a single dose of vehicle (controls) or compound by an oral gavage at the indicated doses. One hour after drug dosing, all rats were injected intraperitoneally with sodium[1-$^{14}$C]-acetate (18.75 μCi/rat in 0.2 ml saline). After 50 minutes, blood samples were taken, plasma obtained by centrifugation, and plasma [$^{14}$C]cholesterol measured after saponification and extraction.

The activities of several representative examples of compounds in accordance with the present invention appear in Tables 1 and 2 below.

TABLE 1

| Example Number | $CSI/IC_{50}$ [μmole/liter] |
|---|---|
| 1 | 0.36 |
| 2 | 0.18 |
| 3 | 0.23 |
| 4 | 0.42 |
| 6 | 0.062 |
| 7 | 0.068 |
| 8 | 0.072 |
| 10 | 0.070 |
| 12 | 0.14 |
| 14 | 0.079 |
| 16 | 0.030 |
| 20 | 0.016 |
| 23 | 0.05 |
| 25 | 0.071 |
| 27 | 0.032 |
| 29 | 0.050 |
| 31 | 0.058 |
| 33 | 0.020 |
| 35 | 0.044 |
| 37 | 0.024 |
| 39 | 0.008 |
| 41 | 0.011 |

TABLE 2

| Example Number | % Inhibition of Cholesterol Synthesis |
|---|---|
| 9 | −55[a] |
| 11 | −41[a] |
| 13 | −67[b] |
| 15 | −55[b] |
| 19 | −72[b] |
| 21 | −67[b] |
| 22 | −59[b] |
| 24 | −54[b] |
| 26 | −60[b] |
| 28 | −64[a] |
| 30 | −64[b] |
| 32 | −25[b] |
| 34 | −57[b] |
| 36 | −68[b] |
| 38 | −67[b] |
| 40 | −68[b] |
| 42 | −69[b] |

[a] 1.5 mg/kg
[b] 1.0 mg/kg

For preparing pharmaceutical compositions from the compounds described by this invention, inert, pharmaceutically acceptable carriers can be either solid or liquid. Solid form preparations include powders, tablets, dispersible granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with finely divided active compound. In tablets, the active compound is mixed with the carrier having the necessary binding properties in suitable proportions and compacted in the shape and size desired.

For preparing suppository preparations, a low-melting wax such as a mixture of fatty-acid glycerides and cocoa butter is first melted, and the active ingredient is dispersed homogeneously therein, as by stirring. The molten homogeneous mixture is then poured into convenient sized molds and allowed to cool and solidify.

The powders and tablets preferably contain 5 to about 70% of the active ingredient. Suitable solid carriers are magnesium carbonate, magnesium stearate, talc, sugar, lactose, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as carrier providing a capsule in which the active component (with or without other carriers) is surrounded by a carrier, which is thus in association with it. Similarly, cachets are included. Tablets, powders, cachets, and capsules can be used as solid dosage forms suitable for oral administration.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions for oral use can be prepared by dissolving the active component in water and adding suitable colorants, flavoring agents, stabilizers, and thickening agents as desired. Aqueous suspensions for oral use can be made by dispersing the finely divided active component in water with viscous material, i.e., natural or synthetic gums, resins, methyl, cellulose, sodium carboxymethyl cellulose, and other well-known suspending agents.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these packaged forms.

In therapeutic use as hypolipidemic or hypocholesterolemic agents, the compounds utilized in the pharmaceutical method of this invention are administered to the patient at dosage levels of from 40 mg to 600 mg per day. For a normal human adult of approximately 70 kg or body weight, this translates to a dosage of from about 0.5 mg/kg to about 8.0 mg/kg of body weight per day.

The dosages, however, may be varied depending upon the requirements of the patient, the severity of the condition being treated, and the compound being employed. Determination of optimum dosages for a particular situation is within the skill of the art.

The following examples illustrate particular methods for preparing compounds in accordance with this invention. These examples are illustrative and are not to be read as limiting the scope of the invention as it is defined by the appended claims.

EXAMPLE 1

Preparation of [4α,6β(E)]-Tetrahydro-4-hydroxy-6-[2-(2-methyl-4-phenyl-3-pyridinyl)ethenyl]-2H-pyran-2-one Step 1: Preparation of Ethyl 1,4-Dihydro-2-methyl-4-phenyl-3-pyridinecarboxylate (E)-3-Phenyl-2-propanol (13.8 ml, 0.11 mol) and ethyl 3-amino-2-butenoate (12.9 g, 0.1 mol) were dissolved in 150 ml of absolute ethanol containing 0.5 ml of piperidine. The mixture was heated under reflux for 18 hours followed by removal of the solvent under vacuum to yield 17.6 g of ethyl 1,4-dihydro-2-methyl-4-phenyl-3-pyridinecarboxylate as a brown viscous oil.

NMR (CDCl$_3$): 7.1$\delta$ (multiplet, 5 protons), 5.8$\delta$ (multiplet, 2 protons), 4.8$\delta$ (triplet, 1 proton), 4.4$\delta$ (doublet, J=5 Hz, 1 proton), 3.98$\delta$ (quartet, J=7 Hz, 2 protons), 2.7$\delta$ (singlet, 3 protons), 1.05$\delta$ (triplet, J=7 Hz, 3 protons).

Step 2: Preparation of Ethyl 2-Methyl-4-phenyl-3-pyridinecarboxylate

To a solution of 0.32 mol ethyl 1,4-dihydro-2-methyl-4-phenyl-3-pyridinecarboxylate in 50 ml of methylene chloride was added 16 g (0.5 mol) of sulfur. The temperature of the well-stirred dark solution was raised over a period of about 30 minutes to 170°–180° C. When the development of hydrogen sulfide had subsided, the reaction mixture was cooled to room temperature, taken up in toluene, and filtered through Celite filter aid. The filtrate was concentrate under vacuum and the residue chromatographed on silica gel, eluting with ethyl acetate/hexane to yield 61.7 g of ethyl 2-methyl-4-phenyl-3-pyridinecarboxylate.

NMR (CDCl$_3$): 8.3$\delta$ (doublet, J=5 Hz, 1 proton), 7.3 (singlet, 5 protons), 6.95$\delta$ (doublet, J=5 Hz 1 proton), 3.80$\delta$ (quartet, J=7 Hz, 2 protons), 2.4$\delta$ (singlet, 3 protons), 0.8$\delta$ (triplet, J=7 Hz, 3 protons).

Step 3: Preparation of 2-Methyl-4-phenyl-3-pyridinemethanol

To a solution of 32.8 g (0.136 mol) of ethyl 2-methyl-4-phenyl-3-pyridine carboxylate in 250 ml of dry methylene chloride at −78° C. under nitrogen was added in a dropwise manner a solution of 300 ml 1M diisobutyl aluminum hydride in methylene chloride. After completion of addition the reaction mixture was stirred at −78° C. for another 90 minutes before it was quenched by the addition of 40 ml of saturated aqueous sodium sulfate solution.

The cooling bath was removed and the mixture stirred for 40 minutes, after which the mixture was filtered and the solvent removed under vacuum.

Flash chromatography on silica gel, eluting with ethyl acetate/hexane yielded 16.2 g of crystalline 2-methyl-4-phenyl-3-pyridinemethanol.

NMR (CDCl$_3$): 8.13$\delta$ (doublet, J=5 Hz, 1 proton), 7.33$\delta$ (singlet, 5 protons), 6.95$\delta$ (doublet, J=5 Hz, 1 proton), 5.4$\delta$ (singlet, 1 proton), 4.53$\delta$ (singlet, 2 protons), 2.63$\delta$ (singlet, 3 protons).

Step 4: Preparation of 2-Methyl-4-phenyl-3-pyridinecarboxaldehyde

Oxalyl chloride (8.5 ml, 0.097 mol) was dissolved in 250 ml of methylene chloride and cooled under a stream of nitrogen to −78° C. Dimethylsulfoxide (15.2 ml, 0.196 mol) was added dropwise to this mixture over a period of three minutes. After five minutes, a solution of 16.2 g (0.081 mol) of 2-methyl-4-phenyl-3-pyridinemethanol in 120 ml of methylene chloride was added in a dropwise manner to the reaction mixture. The resulting mixture was stirred at −78° C. for an additional ten minutes, after which 55 ml of triethylamine was added in one portion. After 20 minutes the cooling bath was removed and the reaction was quenched by the addition of 50 ml of saturated aqueous ammonium chloride solution.

The organic layer was separated, washed twice with 100-ml portions of water, dried over magnesium sulfate, and concentrated under vacuum to yield 2-methyl-4-phenyl-3-pyridinecarboxaldehyde.

NMR (CDCl$_3$): 10.0$\delta$ (singlet, 1 proton), 8.5$\delta$ (doublet, J=5 Hz), 7.4$\delta$ (multiplet, 5 protons), 7.2$\delta$ (doublet, J=5 Hz, 1 proton), 2.8$\delta$ (singlet, 3 protons).

Step 5: Preparation of (E)-Methyl-3-(2-Methyl-4-phenyl-3-pyridinyl)-2-propenoate Methyl (triphenylphosphoranylidene)acetate (30 g) was added to a stirred mixture of 16.0 g (0.081 mol) of 2-methyl-4-phenyl-3-pyridinecarboxaldehyde in 300 ml of methylene chloride. The resulting mixture was stirred at room temperature for 18 hours, after which the mixture was filtered through silica gel and the filtrate concentrated under vacuum. The residue was chromatographed on a silica gel column, eluting with ethyl acetate to yield 18.9 g of (E)-methyl-3-(2-methyl-4-phenyl-3-pyridinyl)-2-propenoate.

NMR (CDCl$_3$): 8.48$\delta$ (doublet, J=5 Hz, 1 proton), 7.66$\delta$ (doublet, J=18 Hz, 1 proton), 7.26$\delta$ (multiplet, 5 protons), 7.06$\delta$ (doublet, J=5 Hz, 1 proton), 5.8$\delta$ (doublet, J=18 Hz, 1 proton), 3.67$\delta$ (singlet, 3 protons), 2.6$\delta$ (singlet, 3 protons).

Step 6: Preparation of (E)-3-(2-Methyl-4-phenyl-3-pyridinyl)-2-propen-1-ol (E)-Methyl-3-(2-Methyl-4-phenyl-3-pyridinyl)-2-propenoate (16.6 g, 0.066 mol) was dissolved in 500 ml of dry methylene chloride and the resulting mixture was cooled to −78° C. under nitrogen. Diisobutyl aluminum hydride ("DIBAL," 145 ml, 1M in methylene chloride) was added dropwise to the vigorously stirred reaction mixture over a period of 15 minutes. When addition was complete, the cooling bath was removed and the mixture was stirred for an additional 15 minutes. After this time the reaction was quenched by the addition of 20 ml of saturated aqueous sodium sulfate solution.

The resulting mixture was filtered through Celite filter aid and the filtrate was concentrated under vacuum to yield 14.3 g of (E)-3-(2-methyl-4-phenyl-3-pyridinyl)-2-propen-1-ol.

NMR (CDCl$_3$): 8.3δ (doublet, J=5 Hz, 1 proton), 7.5δ (multiplet, 5 protons), 7.0δ (doublet, J=5 Hz, 1 proton), 6.5δ (doublet, J=18 Hz, 1 proton), 5.6δ (doublet of doublets, j=18 Hz, J=6 Hz, 1 proton), 4.1δ (multiplet, 2 protons), 2.6δ (singlet, 3 protons).

Step 7: Preparation of (E)-3-(2-Methyl-4-phenyl-3-pyridinyl)-2-propenal

Oxalyl chloride (6.5 ml) was dissolved in 150 ml of dry methylene chloride and the resulting mixture was cooled to −78° C. Dimethylsulfoxide (11.05 ml, 0.143 mol) was added to the vigorously stirred mixture over a period of 2 minutes. The reaction mixture was stirred for 5 minutes and then 0.065 mol of (E)-3-(2-methyl-4-phenyl-3-pyridinyl)-2-propen-1-ol in 150 ml was added dropwise over a period of five minutes.

The resulting mixture was stirred for 15 minutes, after which time the reaction was quenched by the addition of 45 ml of triethylamine. The cooling bath was removed and, after 20 minutes, the mixture was poured onto 100 ml of saturated aqueous ammonium chloride solution. The organic layer was separated, washed twice with 50-ml portions of water, dried over anhydrous magnesium sulfate, and concentrated under vacuum. The residue was purified by flash chromatography over silica gel, eluting with ethyl acetate/hexane to yield the solid product. Recrystallization from ethyl acetate/hexane yielded 12.8 g of (E)-3-(2-methyl-4-phenyl-3-pyridinyl)-2-propenal, mp 98°–99° C.

Step 8: Preparation of (E)-Ethyl-5-hydroxy-7-(2-methyl-4-phenyl-3-pyridinyl)-3-oxo-6-heptenoate Dry tetrahydrofuran (125 ml) was added to 2.7 g of sodium hydride (0.062 mol, 60% in oil) under a stream of nitrogen. The resulting mixture was cooled to 0° C. and ethyl acetoacetate (7.9 ml, 0.062 mol) was added by means of a syringe at a rate slow enough to prevent the reaction temperature from rising. The nearly colorless solution was then stirred at 0° C. for ten minutes before n-butyl lithium (26 ml, 2.4M in hexane) was added by means of a syringe over a period of three minutes.

The pale orange reaction mixture was stirred for an additional 10 minutes, cooled to −78° C., and 12.5 g (0.0565 mol) of (E)-3-(2-methyl-4-phenyl-3-pyridinyl)-2-propenal in 150 ml of absolute tetrahydrofuran was added from a dropping funnel over a period of two minutes. After the addition was complete, the mixture was stirred for ten minutes. Acetic acid (9 ml) was added, the cooling bath was removed, and most of the tetrahydrofuran was removed under vacuum. The residue was partitioned between chloroform and saturated aqueous sodium bicarbonate solution. The organic layer was separated, washed twice with water, dried over anhydrous magnesium sulfate, and concentrated under reduced pressure. Flash chromatography of the residue on silica gel, eluting with ethyl acetate/hexane yielded 17.2 g of crude (E)-ethyl 5-hydroxy-7-(2-methyl-4-phenyl-3-pyridinyl)-3-oxo-6-heptenoate. Recrystallization from ether yielded pure material, mp 83°–84° C.

Step 9: Preparation of [R*,S*(E)]-3,5-Dihydroxy-7-(2-methyl-4-phenyl-3-pyridinyl)-6-heptenoate To a solution of 13.75 g (0.039 mol) of (E)-ethyl 5-hydroxy-7-(2-methyl-4-phenyl-3-pyridinyl)-3-oxo-6-heptenoate and 0.42 g (0.0042 mol) of 2,2-dimethylpropanoic acid in 120 ml of anhydrous tetrahydrofuran under a dry air atmosphere was added 43 ml of triethylborane (1M in tetrahydrofuran) via a syringe in one portion. The resulting yellow solution was stirred at room temperature for five minutes and then cooled to −78° C. Absolute methanol (15 ml) was added, followed by 1.62 g (0.043 mol) of sodium borohydride. The reaction mixture was stirred at −78° C. for seven hours and then poured into a 1:1 mixture of 30% hydrogen peroxide and ice. This mixture was stirred overnight and then partitioned between chloroform and saturated aqueous sodium bicarbonate solution.

The organic layer was separated, washed with water until peroxide free, dried over anhydrous magnesium sulfate, and concentrated under vacuum. Chromatographic purification of the residue on silica gel yielded 9.25 g of [R*,S*(E)]-ethyl-3,5-dihydroxy-7-(2-methyl-4-phenyl-3-pyridinyl)-6-heptenoate, mp 85°–86° C.

Step 10: Preparation of [R*,S*(E)]-3,5-Dihydroxy-7-(2-methyl-4-phenyl-3-pyridinyl)-6-heptenoic acid, sodium salt To 8.90 g (0.025 mol) of [R*,S*(E)]-ethyl-3,5-dihydroxy-7-(2-methyl-4-phenyl-3-pyridinyl)-6-heptenoate in 50 ml of tetrahydrofuran was added exactly 25.2 ml of 1M aqueous sodium hydroxide solution and just enough ethanol to make the reaction mixture single phase. After stirring this mixture for two hours, the organic solvents were removed under reduced pressure. Water (3 ml) was added to the residue and the resulting mixture was extracted with 50 ml of diethyl ether. The water layer was concentrated under vacuum and the residual water removed by azeotropic evaporation twice with toluene yielding [R*,S*(E)-3,5-dihydroxy-7-(2-methyl-4-phenyl-3-pyridinyl)-6-heptenoic acid, sodium salt, mp 130°–135° C. (dec.)

Step 11: Preparation of [4α,6β(E)]-Tetrahydro-4-hydroxy-6-[2-(2-methyl-4-phenyl-3-pyridinyl)ethyl]-2H-pyran-2-one To 0.0232 mol of [R*,S*(E)]-3,5-dihydroxy-7-(2-methyl-4-phenyl-3-pyridinyl)-6-heptenoic acid, sodium salt in 50 ml of water is added dropwise 23.2 ml of 1M hydrochloric acid. The water was evaporated from this mixture under reduced pressure and toluene was added to the residue. The resulting mixture was evaporated to dryness under reduced pressure to yield a white solid. Toluene (500 ml) was added to this solid residue and the mixture heated under reflux in an apparatus equipped with a Dean Stark trap. After 60 minutes the heating was discontinued and the organic solvent removed under reduced pressure. The residue was taken up in chloroform and washed with sodium bicarbonate solution. The organic layer was collected, dried over magnesium sulfate, and concentrated under vacuum to produce [4α,6β(E)]-tetrahydro-4-hydroxy-6-[2-(2-methyl-4-phenyl-3-pyridinyl)ethenyl]-2H-pyran-2-one as an off-white solid. Recrystallization from chloroform/hexane yielded pure material, mp 164°–165° C.

NMR (CDCl$_3$): 8.38δ (doublet, J=5 Hz, 1 proton), 7.3δ (multiplet, 5 protons), 7.08δ (doublet, J=5 Hz, 1 proton), 6.60δ (doublet, J=16 Hz, 1 proton), 5.46δ (doublet of doublets, J=6 Hz, J=16 Hz, 1 proton), 5.2δ (multiplet, 1 proton), 4.2δ (multiplet, 1 proton), 3.2δ (singlet, 1 proton), 2.7-2.55δ (multiplet, 2 protons), 2.60δ (singlet, 3 protons), 1.8δ (multiplet, 1 proton), 1.6δ (multiplet, 1 proton).

Infrared spectrum, principle absorptions at 3200, 1739, 1585, 1249, 1070, and 1042 reciprocal centimeters.

EXAMPLE 2

Preparation of
[4α,6β(E)]-6-[2-(2,6-Dimethyl-4-phenyl-3-pyridinyl)ethenyl]tetrahydro-4-hydroxy-2H-pyran-2-one Employing the method of Example 1, but using (E)-4-phenyl-3-buten-2-one instead of transcinammaldehyde in Step 1, there was obtained [4α,6β(E)]-6-[2-(2,6-dimethyl-4-phenyl-3-pyridinyl)ethenyl]tetrahydro-4-hydroxy-2H-pyran-2-one, mp 171°-172° C.

Analyzed for $C_{20}H_{21}NO_3$: Calculated: C, 74.28%; H, 6.55%; N, 4.33%. Found: C, 73.91%, H, 6.42%; N, 4.06%.

NMR (CDCl$_3$): 7.3δ (multiplet, 5 protons), 6.96δ (singlet, 1 proton), 6.57δ (doublet, J=16 Hz, 1 proton), 5.43δ (doublet of doublets, J=6 Hz, J=16 Hz, 1 proton), 5.15δ (multiplet, 1 proton), 4.23δ (multiplet, 1 proton), 2.6δ (multiplet, 2 protons), 2.59δ singlet, 3 protons), 2.54δ (singlet, 3 protons), 1.8δ (multiplet, 1 proton), 1.65δ (multiplet, 1 proton).

Infrared spectrum: Principle absorptions at 1737, 1590, 1230, 1066, 1033, 068, and 709 reciprocal centimeters.

EXAMPLE 3

Preparation of
[R*,S*(E)]-7-(2,6-dimethyl-4-phenyl-3-pyridinyl)-3,5-dihydroxy-6-heptenoic acid, sodium salt

[4α,6β(E)]-6-[2-(2,6-Dimethyl-4-phenyl-3-pyridinyl)ethyl]tetrahydro-4-hydroxy-2H-pyran-2-one, 0.89 g (0.00275 mol) was dissolved in 5 ml of tetrahydrofuran and 2.75 ml of 1M aqueous sodium hydroxide solution was added, together with enough ethanol to render the reaction mixture single phase. After stirring this mixture 90 minutes at room temperature, the solvents were removed under vacuum. Twice, toluene was added to the residue and evaporated to dryness to remove the last traces of water to yield [R*,S*(E)]-7-(2,6-dimethyl-4-phenyl-3-pyridinyl)-3,5-dihydroxy-6-heptenoic acid, sodium salt, mp 115°-120° C. (dec.)

EXAMPLE 4

Preparation of
trans-Tetrahydro-4-hydroxy-6-[2-(2-methyl-4-phenyl-3-pyridinyl)ethyl]-2H-pyran-2-one Step 1: Preparation of (E)-Methyl 3-(2-methyl-4-phenyl-3-pyridinyl)-2-propenoate The procedure of Steps 1-5 of Example 1 were used to prepare the title compound.

Step 2: Preparation of Methyl 2-methyl-4-phenyl-3-pyridinepropanoate (E)-Methyl 3-(2-methyl-4-phenyl-3-pyridinyl)-2-propenoate (7.10 g, 0.028 mol) was dissolved in 500 ml of ethanol under a nitrogen atmosphere. Palladium on activated charcoal (0.14 g, 10%) was added in one portion. The nitrogen atmosphere was evacuated, and hydrogen was introduced. After vigorous shaking for 40 hours, the reaction mixture was filtered under a stream of nitrogen and evaporated under reduced pressure to yield 7.18 g of methyl 2-methyl-4-phenyl-3-pyridinepropanoate.

NMR (CDCl$_3$): 8.3δ (doublet, J=5 Hz, 1 proton), 7.3δ (multiplet, 5 protons), 6.9δ (doublet, J=5 Hz, 1 proton), 3.55δ (singlet, 3 protons), 2.9δ (multiplet, 2 protons), 2.6δ (singlet, 3 protons), 2.3δ (multiplet, 2 protons).

Steps 3: Preparation of 2-Methyl-4-phenyl-3-pyridine propanol

Methyl 2-methyl-4-phenyl-3-pyridinepropanoate (1.00 g, 3.92 mmol) was dissolved in 50 ml of methylene chloride under a nitrogen atmosphere. The clear solution was cooled in a dry-ice/acetone bath and 4.0 ml of 1M diisobutyl aluminum hydride in methylene chloride was added dropwise. The reaction mixture was stirred at −78° C. for two hours, after which time the reaction was quenched by the addition of 10 ml of saturated sodium sulfate solution. The cooling bath was removed and after an additional 30 minutes the suspension was filtered, dried over anhydrous magnesium sulfate, and concentrated under vacuum. The crude product was purified by flash chromatography on silica gel, eluting with ethyl acetate/hexane.

NMR (CDCl$_3$): 9.5δ (singlet, 1 proton), 8.3δ (doublet, J=5 Hz, 1 proton), 7.3δ (multiplet, 5 protons) 6.9δ (doublet, J=5 Hz, 1 proton), 2.7δ (multiplet, 2 protons), 2.6δ (singlet, 3protons), 2.4δ (multiplet, 2 proton).

Step 4: Preparation of
trans-Tetrahydro-4-hydroxy-6-[2-(2-methyl-4-phenyl-3-pyridinyl)ethyl]-2H-pyran-2-one Employing the general method of Steps 7-11 of Example 1, the 2-methyl-4-phenyl-3-pyridine propanol from Step 2 above was converted to trans-tetrahydro-4-hydroxy-6-[2-(2-methyl-4-phenyl-3-pyridinyl)ethyl]-2H-pyran-2-one, mp 107°-108° C.

Analyzed for $C_{19}H_{21}NO_3$: Calculated: C, 73.29%; H, 6.80%; N, 4.50%. Found: C, 73.03%; H, 6.59%; N, 4.48%.

NMR (CDCl$_3$): 8.30δ (doublet, J=5 Hz, 1 proton), 7.3δ (multiplet, 5 protons), 7.0δ (doublet, J=5 Hz, 1 proton), 4.55δ (multiplet, 1 proton), 4.3δ (multiplet, 1 proton), 2.7δ (multiplet, 2 protons), 2.60δ (singlet, 3 protons), 1.8-1.4δ (multiplet, 4 protons).

Infrared spectrum: Principle absorptions at 1735, 1587, 1465, 1250, 1050, and 706 reciprocal centimeters.

EXAMPLE 5

Preparation of
[2α,4β(E)]-4-(4-fluorophenyl)-2,6-dimethyl-5-[2-(tetrahydro-4-hydroxy-6-oxo-2-pyran-2-yl)ethenyl]-3-pyridinecarbonitrile Employing the general method of Example 1, the title compound was prepared, mp 155°-156° C.

Analyzed for $C_{21}H_{19}FN_2O_3$: Calculated: C, 68.84%; H, 5.23%, N, 7.65%. Found: C, 68.76%; H, 5.24%; N, 7.61%.

NMR (CDCl$_3$): 7.28-7.13δ (multiplet, 4 protons), 6.42δ (doublet, J=16 Hz, 1 proton), 5.43δ (doublet of doublets, J=16 Hz, J=6 Hz, 1 proton), 5.15δ (multiplet, 1 proton), 4.2δ (multiplet, 1 proton), 2.78δ (singlet, 3 protons), 2.66δ (multiplet, 2 protons), 2.63δ (singlet, 3 protons), 1.8-1.4 (multiplet, 2 protons).

Infrared spectrum: Principle absorptions at 3400, 2917, 2228, 1733, 1607, 1549, and 1242 reciprocal centimeters.

EXAMPLE 6

Preparation of
[R*,S*(E)]-7-[5-Cyano-4-(4-fluorophenyl)-2,6-dimethyl-3-pyridinyl]-3,5-dihydroxy-6-heptenoic acid, sodium salt Using the method of Example 1 above, the title compound was prepared.

Infrared spectrum: Principle absorptions at 3450, 2227, 1632, 1511, and 1161 reciprocal centimeters.

Mass spectrum: M/z (% base peak): 429 (100), 407 (31), 385 (17), 279 (15), 267 (11), 251 (21).

EXAMPLE 7

Preparation of
[4α,6β(E)]-6-[2-[4-(4-Fluorophenyl)-2,6-dimethyl-3-pyridinyl]ethenyl]tetrahydro-4-hydroxy-2H-pyran-2-one Using the general methods of Example 1, the title compound was prepared, mp 193°–194° C.

EXAMPLE 8

Preparation of
[R*,S*(E)]-7-[4-(4-Fluorophenyl)-2,6-dimethyl-3-pyridinyl]-3,5-dihydroxy-6-heptenoic acid, sodium salt Using the general method of Example 1, the title compound was prepared, mp 100°–110° C.

EXAMPLE 9

Preparation of
[2α,4β(E)]-4-(4-fluorophenyl)-6-methyl-2-(1-methylethyl)-5-[2-(tetrahydro-4-hydroxy-6-oxo-2H-pyran-2-yl)ethenyl]-3-pyridinecarboxylic acid Step 1

A solution of 198 g (1.37 mol) 4-methyl-3-oxo-pentenoic acid methylester and 147 ml (1.37 mol) 4-fluorobenzaldehyde in 500 ml toluene was heated to reflux in the presence of 4 ml piperidine, continuously removing water by Dean Stark. The mixture was concentrated and distilled at oil pump vacuum, yield 251 g colorless oil, bp 170°–180° C./0.1 Torr.

Step 2

Employing the general method of Example 1, but using 2-[(4-fluorophenyl)methylene]-4-methyl-3-oxopentanoic acid methyl ester instead of trans-cinnamaldehyde in Step 1, there was obtained the title compound, mp 131°–132° C.

Analyzed for $C_{24}H_{26}FNO_5$: Calculated: C, 67.43%; H, 6.13%; N, 3.28%. Found: C, 67.36%; H, 5.82%; N, 3.06%.

EXAMPLE 10

Preparation of
[R*,S*-(E)]-5-(6-carboxy-3,5-dihydroxy-1-hexenyl)-4-(4-fluorophenyl)-6-methyl-2-(1-methylethyl)-, 3-methyl ester, 3-pyridinecarboxylic acid, monosodium salt Using the general method of Example 1, the title compound was prepared, mp 220°–225° C.

Analyzed for $C_{24}H_{27}FNO_6Na$: Calculated: C, 61.67%; H, 5.82%; N, 3.00%. Found: C, 61.62%; H, 5.92%; N, 2.80%.

EXAMPLE 11

Preparation of
[4α,6β-(E)]-4-(4-fluorophenyl)-2,6-dimethyl-5-[2-(tetrahydro-4-hydroxy-6-oxo-2H-pyran-2-yl)ethenyl]-, ethyl ester, 3-pyridinecarboxylic acid Employing the general method of Example 1, the title compound was prepared, mp 123°–124° C.

Analyzed for $C_{23}H_{24}FNO_5$: Calculated: C, 66.82%; H, 5.85%; N, 3.39%. Found: C, 67.05%; H, 5.73%; N, 3.23%.

EXAMPLE 12

Preparation of
[R*,S*-(E)]-5-(6-carboxy-3,5-dihydroxy-1-hexenyl)-4-(4-fluorophenyl)-2,6-dimethyl-, 3-ethyl ester, 3-pyridinecarboxylic acid, monosodium salt Using the method of Example 1 above, the title compound was prepared, mp 220°–230° C. (dec).

Infrared spectrum: Principle absorptions at 3500, 1728, 1606, 1578, 1511, 1404, 1225 reciprocal centimeters.

EXAMPLE 13

Preparation of
[2α,4β-(E)]-4-(4-fluorophenyl)-2,6-bis(1-methylethyl)-5-[2-(tetrahydro-4-hydroxy-6-oxo-2H-pyran-2-yl)ethenyl]-3-pyridinecarboxylic acid, methyl ester Employing the general method of Example 1, the title compound was prepared.

Analyzed for $C_{26}H_{30}FNO_5$: Calculated: C, 68.56%; H, 6.64%; N, 3.07%. Found: C, 68.56%; H, 6.61%; N, 2.87%.

EXAMPLE 14

Preparation of
[R*,S*-(E)]-5-(6-carboxy-3,5-dihydroxy-1-hexenyl)-4-(4-fluorophenyl)-2,6-bis-1-methylethyl)-, methyl ester-3-pyridinecarboxylic acid, sodium salt Employing the general procedure of Example 1, the title compound was obtained.

Analyzed for $C_{26}H_{31}FNO_6Na$: Calculated: C, 63.02%; H, 6.31%; N, 2.83% Found: C, 64.20%; H, 6.43%; N, 2.53%

Infrared spectrum: Principle absorptions at 3500, 2967, 2871, 1734, 1605, 1580, 1511, 1160 reciprocal centimeters.

EXAMPLE 15

Preparation of
[4α,6β(E)]-6-[2-(4-fluorophenyl)-2,6-bis(1-methylethyl)-3-pyridinyl]ethenyl]tetrahydro-4-hydroxy-2H-pyran-2-one Step 1: Preparation of Dimethyl 2,6-diisopropyl-4(4-fluorophenyl)-3,5-pyridinecarboxylate The procedure of Steps 1–2 of Example 1 were used to prepare the title compound.

Step 2: Preparation of Methyl 2,6-diisopropyl-4-(4-fluorophenyl)-3,5-pyridinedicarboxylate A suspension of 5.9 g (0.108 mol) sodium methanolate and 40.3 g dimethyl 2,6-diisopropyl-4-(4-fluorophenyl)-3,5-pyridinedicarboxylate in 250 ml dimethylformamide was heated to reflux. After 10 min 2.5 ml H₂O was added and reflux was continued for 16 hours. The reaction mixture was cooled to room temperature and partitioned between 100 ml 1N sodium hydroxide and ether. The aqueous layer was acidified with dilute citric acid, and then extracted extensively with chloroform. The combined organic layers were dried over anhydrous magnesium sulfate, filtered, and evaporated. Yield: 22.4 g brown solid.

NMR (CDCl₃): δ6.7–7.3 (m, 4H); 3.42 (s, 3H); 2.8–3.3 (m, 2H); 1.24 (d, J=7 Hz, 12H).

Step 3: Preparation of Methyl 2,6-diisopropyl-4(4-fluorophenyl)-3-pyridinecarboxylate 15.0 g (0.042 mol) of methyl 2,6-diisopropyl-4(4-fluorophenyl)-3,5-dicarboxylate was heated to 250°–290° C. for 15 min. The reaction mixture was then cooled to room temperature and partitioned between 1N sodium hydroxide and Et₂O. The ether layer was dried over anhydrous magnesium sulfate, filtered, and evaporated. Yield: 4.32 g colorless oil.

NMR (CDCl₃): δ6.8–7.35 (m, 4H); 6.87 (s, 1H); 3.54 (s, 3H); 2.85–3.25 (m, 2H); 1.27 (d, J=7 Hz, 12H).

Step 4: Preparation of title compound

Employing the general method of Steps 3–11 of Example 1, the methyl 2,6-diisopropyl-4(4-fluorophenyl)-3-pyridinecarboxylate from Step 2 above was converted to the title compound, mp 127°–128° C.

Analyzed for C₂₄H₂₈FNO₃: Calculated: C, 72.52%; H, 7.10%; N, 3.52%. Found: C. 72.63%; H, 6.99%; N, 3.64%.

EXAMPLE 16

Preparation of [R*,S*(E)]-7-[4-(4-fluorophenyl)-2,6-bis(1-methylethyl)-3-pyridinyl]-3,5-dihydroxy-6-heptenoic acid, monosodium salt Using the general method of Example 3, the title compound was obtained starting from title compound of Example 15, mp 235°–240° C. (dec.).

Analyzed for C₂₄H₂₉FNO₄Na Calculated: C, 65.89%; H, 6.68%; N, 3.20%. Found: C, 66.17%; H, 6.70%; N, 3.23%.

EXAMPLE 17

Preparation of N-oxide, [4α,6β(E)]-6-[2[4-(4-fluorophenyl)-2,6-bis(1-methylethyl)-3-pyridinyl]ethenyl]tetrahydro-4-hydroxy-2H-pyran-2-one Preparation of title compound: 0.08 g (2.0 mmol) of title compound of Example 15 was dissolved in 5 ml dichloromethane; 0.70 g (~4 mmol) meta-chloroperbenzoic acid was added and the resulting mixture was heated to reflux for 45 minutes. The cooled reaction mixture was partitioned between aqueous sodium bicarbonate solution and ethyl acetate. The organic layer was dried over anhydrous magnesium sulfate, filtered, and evaporated. The white, crystalline residue was recrystallized from ethyl acetate/hexane and yielded 0.64 g white powder, mp 178°–179° C.

EXAMPLE 18

Preparation of [4α,6β(E)]-6-[2-(4-(4-fluorophenyl)-2,6-dimethyl-3-pyridinyl]ethenyl]tetrahydro-4-hydroxy-2H-pyran-2-one, N-oxide Preparation of title compound: Using the general procedure of Example 17, the title compound was obtained starting from the title compound in Example 7, mp 208°–209° C.

EXAMPLE 19

Preparation of [4α,6β(E)]-6-[2-[4-(4-fluorophenyl)-6-methyl-2-(1-methylethyl)-3-pyridinyl]ethenyl]tetrahydro-4-hydroxy-2H-pyran-2-one Using the general method of Example 1, the title compound was prepared, mp 164.5°–166.0° C.

EXAMPLE 20

Preparation of [R*,S*-(E)]-7-[4-(4-fluorophenyl)-6-methyl-2-(1-methylethyl)-3-pyridinyl-3,5-dihydroxy-6-heptenoic acid, sodium salt Using the general method of Example 3, the title compound was prepared, mp 195°–205° C. dec.

Analyzed for C₂₂H₂₅FNO₄Na: Calculated: C, 64.54%; H, 6.16%; N, 3.42%. Found: C, 64.69%; H, 6.30%; N, 2.92%.

EXAMPLE 21

Preparation of [R*,S*-(E)]-7-[4-(4-fluorophenyl)-6-methyl-2-(1-methylethyl)-3-pyridinyl]-3,5-dihydroxy-6-heptenoic acid, hemicalcium salt The title compound of Example 20 (2.20 g, 0.00541 mol) was dissolved in 8 ml of water and 0.40 g (0.00271 mol) of CaCl₂.2H₂O was added. As precipitate immediately formed. The water was decanted off and 10 ml of water was added. This water was decanted off and the residue was taken up in methanol/toluene and this mixture was concentrated under reduced pressure to remove the last traces of water to yield the title compound, mp 200°–209° C. dec.

Analyzed for C₂₂H₂₅FNO₄.½Ca: Calculated: C, 65.01%; H, 6.20%; N, 3.45%. Found: C, 64.58; H, 6.20%; N, 3.10%.

EXAMPLE 22

Preparation of [4α,6β(E)]-6-[2-[4-(4-fluorophenyl)-6-methyl-2-(trifluoromethyl)-3-pyridinyl]ethenyl]tetrahydro-4-hydroxy-2H-pyran-2-one Step 1: Preparation of Benzyl 3-amino crotonate Benzylacetoacetate (100 g, 0.52 mol) was heated to 45° C. in a 500-ml three-neck flask equipped with a thermometer, gas inlet tube, and a magnetic stirrer. Ammonia gas was bubbled through the solution periodically, keeping the temperature at 60° C. for six hours. The resulting material was taken up in diethylether (600 ml), dried (MgSO₄), and concentrated under reduced pressure. Distillation (132° C., 1.0 mm) yielded the title compound.

Step 2: 4-(4-Fluorophenyl)-1,4-dihydro-2-methyl-6-(trifluoromethyl)-3,5-pyridinedicarboxylic acid, 5-ethyl 3-phenylmethyl ester Ethyl-4,4,4-trifluoroacetoacetate (9.4 g, 0.0152 mol) and benzyl-3-amino-crotonate (9.8 g, 0.512 mol) were dissolve in 150 ml of absolute ethanol containing 0.5 ml of piperidine. The mixture was heated under reflux for 14 hours followed by removal of the solvent. The residue was taken up in ethyl acetate (500 ml), washed with 50% saturated NaHSO3 (1×160 ml), washed with brine (1×160 ml), dried (MgSO4), and concentrated under reduced pressure. The residual oil was taken up in dichloromethane (250 ml), DMAP (0.57 g), acetic anhydride (7.6 ml), and triethylamine (7.9 ml) were added and the resulting solution was stirred (25° C.) for 24 hours. The resulting solution was washed with brine (1×100 ml), washed with saturated NaHCO3 (1×100 ml), washed again with brine (1×100 ml), dried (MgSO4), concentrated under reduced pressure, and chromatographed on silica (90:10 hexane:ethyl acetate) to yield the title compound.

$^1$H NMR (90 MHz, CDCl$_3$): δ6.7–7.3 (m, 9H), 6.20 (br s, 1H), 5.00 (s, 2H), 4.10 (q, 2H), 2.34 (s, 3H), 1.18 (t, 3H).

Step 3: Preparation of 4-(4-Fluorophenyl)-2-methyl-6-(trifluoromethyl)-3,5-pyridinedicarboxylic acid, 5-ethyl 3-phenylmethyl ester The procedure of Step 2 of Example 1 was used to prepare the title compound.

Step 4: Preparation of 4-(4-Fluorophenyl)-2-methyl-6-(trifluoromethyl)-3,5-pyridinedicarboxylic acid, 5-ethyl ester A mixture of 4-4-(fluorophenyl)-2-methyl-6-trifluoromethyl)-3,5-pyridinedicarboxylic acid, 5-ethyl 3-phenyl methyl ester (33.1 g) and 20% Pd/C (2.0 g) in THF/MeOH (1.1, 600 ml) was hydrogenated at 50 psi for 18 hours. The resulting mixture was filtered through celite and concentrated under reduced pressure to yield 25.0 g of the title compound.

$^1$H NMR (90 MHz, CDCl$_3$): δ7.0–7.4 (m, 4H), 3.98 (q, 2H), 2.67 (s, 3H), 1.00 (t, 3H)

Step 5: Preparation of [4α,6β(E)]-6-[2-[4-(4-Fluorophenyl)-6-methyl-2-(trifluoromethyl)-3-pyridinyl]ethenyl]tetrahydro-4-hydroxy-2H-pyran-2-one The procedure of Steps 3–4 of Example 15 was used to prepare the title compound, mp 176°–179° C.

EXAMPLE 23

Preparation of [R*,S*-(E)]-7-[4-(4-fluorophenyl)-6-methyl-2-(trifluoromethyl)-3-pyridinyl]-3,5-dihydroxy-6-heptenoic acid, monosodium salt Using the general method of Example 3, the title compound was prepared, mp 185°–200° C., (dec).

EXAMPLE 24

Preparation of [4α,6β(E)]-6-[2-[6-difluoro-methyl)-4-(4-fluorophenyl)-2-(trifluoromethyl)-3-pyridinyl]ethenyl]tetrahydro-4-hydroxy-2H-pyran-2-one Using the general method of Example 15, the title compound was prepared, mp 158°–160° C.

EXAMPLE 25

Preparation of [R*,S*-(E)]-7-[6-(difluoromethyl)-4-(4-fluorophenyl)-2-(trifluoromethyl)-3-pyridinyl]-3,5-dihydroxy-6-heptenoic acid, monosodium salt Using the general method of Example 3, the title compound was prepared, mp 210°–220° C.

Analyzed for C$_{20}$H$_{16}$F$_6$NO$_4$Na: Calculated: C, 50.98%; H, 3.42%; N, 2.97%. Found: C, 51.39%; H, 3.72%; N, 2.62%.

EXAMPLE 26

[4α,6β(E)]-6-[2-[2,6-diethyl-4(4-fluorophenyl)-3-pyridinyl]ethenyl]tetrahydro-4-hydroxy-2H-pyran-2-one Using the general method of Example 15, the title compound was prepared, mp 148°–150° C.

Analyzed for C$_{22}$H$_{24}$FNO$_3$: Calculated: C, 71.53%; H, 6.55%; N; 3.79%.

Found: C, 71.40%; H, 6.44%, N; 3.59%.

EXAMPLE 27

Preparation of [R*,S*-(E)]-7-[2,6-diethyl-4-4-(fluorophenyl)-3-pyridinyl]-3,5-dihydroxy-6-heptenoic acid, monosodium salt Using the general method of Example 3, the title compound was prepared, mp 175°–185° C. (dec.).

EXAMPLE 28

[4α,6β(E)]-6-[2-[2-(4-fluorophenyl)-4,6-dimethyl-3-pyridinyl]ethenyl]tetrahydro-4-hydroxy-2H-pyran-2-one

Step 1: Preparation of 4-Fluoro-β-oxobenzenepropanoic acid, ethyl ester

A solution of 4-fluoroacetophenone (100 g, 7.239 mol) in dry THF (100 ml) was added dropwise over 2.5 hours to a refluxing slurry of hexane-washed NaH (68.3 g, 60% oil dispersion, 1.708 mol) and diethyl carbonate (176.0 ml, 1.453 mol) in dry THF (300 ml). This solution was refluxed an additional 0.5 hours, cooled (0° C.), and a solution of ethanol (50 ml) in dry THF (150 ml) was added to quench the excess NaH. 300 ml of water and 100 ml of acetic acid were added, and this mixture was extracted with ethyl acetate (3×300 ml). The combined organics were washed with saturated NaHCO3 (1×500 ml), washed with brine (2×500 ml), dried (MgSO4), concentrated under reduced pressure, and distilled at 10 mm to yield 146.3 g of the title compound.

$^1$H NMR (90 MHz, CDCl$_3$): δ7.90 (m, 2H), 7.10 (m, 2H), 4.17 (q, 2H), 3.93 (s, 2H), 1.30 (t, 3H).

Step 2: Preparation of α-Ethylidene-4-fluoro-β-oxo-benzenepropanoic acid, ethyl ester The procedure of Step 1 of Example 9 was used to prepare the title compound.

Step 3: Preparation of [4α,6β(E)]-6-[2-[2-(4-fluorophenyl)-4,6-dimethyl-3-pyridinyl]ethenyl]tetrahydro-4-hydroxy-2H-pyran-2-one The procedure of Steps 2–5 of Example 22 were used to prepared the title compound, mp 145°–147° C.

Analyzed for $C_{20}H_{20}FNO_3$: Calculated: C, 70.37%; H, 5.91%; N, 4.10%. Found: C, 70.70%; H, 5.95%; N, 4.14%.

EXAMPLE 29

Preparation of [R*,S*-(E)]-7-[2-(4-fluorophenyl)-4,6-dimethyl-3-pyridinyl]-3,5-dihydroxy-6-heptenoic acid, monosodium salt Using the general method of Example 3, the title compound was prepared, mp 95°–115° C.

Analyzed for $C_{20}H_{21}FNO_4Na$: Calculated: C, 62.99%; H, 5.55%; N, 3.67%. Found: C, 63.33%; H, 5.67%; N, 3.45%.

EXAMPLE 30

Preparation of [4α,6β(E)]-6-[2-[4-(4-fluorophenyl)-2-(1-methylethyl)-6-phenyl-3-pyridinyl]ethenyl]tetrahydro-4-hydroxy-2H-pyran-2-one Using the general method of Example 1, the title compound was prepared, mp 172.5°–174° C.

Analyzed for $C_{27}H_{26}FNO_3$: Calculated: C, 75.16%; H, 6.07%; N, 3.25%. Found: C, 74.81%; H, 6.02%; N, 3.11%.

EXAMPLE 31

Preparation of [R*,S*-(E)]-7-[2-[4-(4-fluorophenyl)-2-(1-methylethyl)-6-phenyl-3-pyridinyl]ethenyl]-3,5-dihydroxy-6-heptenoic acid, monosodium salt Using the general method of Example 3, the title compound was prepared, mp 185° C. (dec.).

Analyzed for $C_{27}H_{27}FNO_4Na$: Calculated: C, 68.78%; H, 5.77%; N, 2.97%. Found: C, 68.80%; H, 6.03%; N, 2.72%.

EXAMPLE 32

Preparation of [2α,4α(E)]-4-(4-fluorophenyl)-2,6-bis(1-methylethyl)-n-propyl-5-[2-(tetrahydro-4-hydroxy-6-oxo-2H-pyran-2-yl)ethenyl]-3-pyridinecarboxamide

Step 1: Preparation of 4-(4-Fluorophenyl)-5-(3-hydroxy-2-propenyl)-2,6-bis(1-methylethyl)-3-pyridinecarboxylic acid, methyl ester The procedure of Steps 1–6 of Example 1 was used to prepare the title compound.

Step 2: Preparation of 4-(4-Fluorophenyl)-5-(3-hydroxy-2-propenyl)-2,6-bis(1-methylethyl)-3-pyridinecarboxylic acid A solution of 4-(4-Fluorophenyl)-5-(3-hydroxy-2-propenyl)-2,6-bis(1-methylethyl)-3-pyridinecarboxylic acid, methyl ester (7.5 g, 0.0202 mol) and KOH (3.66 g, 0.0652 mol) in n-butanol was refluxed for 72 hours followed by concentration of the butanol under reduced pressure. The residue was partitioned between water (250 ml) and diethylether (100 ml). The aqueous layer was acidified (citric acid) and extracted with chloroform (3×150 ml). The organic layer was dried ($MgSO_4$) and concentrated to yield 4.0 g of the title compound.

$^1H$ NMR (90 MHz, $CDCl_3$): δ7.10 (m, 4H), 6.24 (d, 1H), 5.36 (dt, 1H), 3.81 (br s, 2H), 2.90–3.5 (br m, 2H), 1.30 (d, 6H), 1.24 (d, 6H).

Step 3: Preparation of 4-(4-Fluorophenyl)-5-(3-hydroxy-2-propenyl)-2,6-bis(1-methylethyl)-N-propyl-3-pyridinecarboxamide To a stirring solution of 4-(4-fluorophenyl)-5-(3-hydroxy-2-propenyl)-2,6-bis(1-methylethyl)-3-pyridinecarboxylic acid (4.0 g, 0.0112 mol) was added 1.51 g of 1-hydroxybenzotriazole (0.0112 mol) followed by 2.31 g of DCC (0.0112 mol). The resulting mixture was stirred 25 minutes, then 1.84 ml of n-propylamine (0.0224 mol) was added. The resulting mixture was stirred for 72 hrs and then was taken up in ethyl acetate (500 ml), filtered, washed with water (2×250 ml), washed with 30% saturated $NaHCO_3$ (1×150 ml), washed with brine (1×150 ml), dried ($MgSO_4$), concentrated under reduced pressure, and chromatographed on silica (1:1 hexane:ethyl acetate) to yield 1.65 g of the title compound.

$^1H$ NMR (90 MHz, $CDCl_3$): δ7.0 (m, 4H), 6.25 (d, 1H), 5.33 (dt, 1H), 3.92 (t, 2H), 3.20 (m, 2H), 2.95 (t, 2H), 1.25 (overlapping t, 12 h; m, 2H), 0.66 (t, 3H).

Step 4: Preparation of [2α,4β(E)]-4-(4-fluorophenyl)-2,6-bis(1-methylethyl)-n-propyl-5-[2-(tetrahydro-4-hydroxy-6-oxo-2H-pyran-2-yl)ethenyl]-3-pyridinecarboxamide The procedure of Steps 7–11 of Example 1 was used to prepare the title compound, mp 215°–217° C.

Analyzed for $C_{28}H_{31}5FN_2O_4$: Calculated: C, 69.69%; H, 7.31%; N, 5.81%. Found: C, 69.41%; H, 7.32%; N, 5.89%.

EXAMPLE 33

Preparation of [R*,S*-(E)]-7-[4-(4-fluorophenyl)-2,6-bis(1-methylethyl)-5-[(propylamino)carbonyl]-3-pyridinyl]-3,5-dihydroxy-6-heptenoic acid, monosodium salt Using the general method of Example 3, the title compound was prepared, mp 220°–235° C.

Analyzed for $C_{28}H_{36}FN_2O_5Na$: Calculated: C, 64.35%; H, 6.94%; N, 5.36%. Found: C, 63.68%; H, 6.95%; N, 5.23%.

EXAMPLE 34

Preparation of [2α,4β(E)]-2,6-diethyl-4-(4-fluorophenyl)-5-[2-(tetrahydro-4-hydroxy-6-oxo-2H-pyran-2-yl)ethenyl]-3-pyridinecarboxylic acid, methyl ester Using the general method of Example 9, the title compound was prepared, mp 105°–108° C.

Analyzed for $C_{24}H_{26}FNO_5$: Calculated: C, 67.43%; H, 6.13%; N, 3.28%. Found: C, 67.37%; H, 6.31%; N, 3.12%.

EXAMPLE 35

[R*,S*-(E)]-5-(6-carboxy-3,5-dihydroxy-1-hexenyl)-2,6-diethyl-4-(4-fluorophenyl)-, methyl ester, 3-pyridinecarboxylic acid, monosodium salt Using the general method of Example 3, the title compound was prepared, mp 195°–205° C. (dec).

Analyzed for $C_{24}H_{27}FNO_6Na$: Calculated: C, 61.67%; H, 5.82%; N, 3.00%. Found: C, 61.70%; H, 6.19%; N, 2.76%.

EXAMPLE 36

Preparation of [4α,6β(E)]-6-[2-[2,6-diethyl-4-(4-fluorophenyl)-5-hydroxymethyl)-3-pyridinyl]ethenyl]tetrahydro-4-hydroxy-2H-pyran-2-one

Step 1: Preparation of 2,6-Diethyl-4-(4-fluorophenyl)-5-(hydroxymethyl)-3-pyridinecarboxylic acid, methyl ester The procedures of Steps 1–3 of Example 1 are used to prepare the title compound.

Step 2: Preparation of 2,6-Diethyl-4-(4-fluorophenyl)-5-[[(tetrahydro-2H-pyran-2-yl)oxy]methyl]-3-pyridinecarboxylic acid, methyl ester A solution of 2,6-diethyl-4-(4-fluorophenyl)-5-(hydroxymethyl)-3-pyridinecarboxylic acid, methyl ester (10.0 g, 0.0315 mol), dihydropyran (4.3 ml, 0.0473 mol) and 6.17 g of p-toluene sulfonic acid was stirred (25° C.) for 24 hours, taken up in dichloromethane (400 ml), washed with saturated $NaHCO_3$ (1×170 ml), washed with brine (1×170 ml), dried ($MgSO_4$), and chromatographed on silica (85:15 hexane:ethyl acetate) to yield 11.1 g of the title compound.

$^1$H NMR (90 MHz, $CDCl_3$): δ6.80–7.30 (m, 4H), 4.46 (d, 1H), 4.35 (br s, 1H), 3.95 (d, 1H), 3.41 (overlapping t, 2H, s; 3H), 2.90 (q, 2H), 270 (q, 2H), 1.10–1.70 (m, 12H).

Step 3: Preparation of Ethyl 7-[2,6-diethyl-4-(4-fluorophenyl)-5-[[(tetrahydro-2H-pyran-2-yl)oxy]methyl]-3-pyridinyl]-δ-hydroxy-β-oxo-6-heptenoate The procedures of Steps 4–8 of Example 1 were used to prepare the title compound from methyl-2,6-diethyl-4-[4-fluorophenyl]-5-tetrahydro-pyranoxy-methyl-3-pyridinecarboxyate.

Step 4: Preparation of Ethyl 7-[2,6-diethyl-4-(4-fluorophenyl)-5-hydroxymethyl)-3-pyridinyl]-δ-hydroxy-β-oxo-6-heptenoate A solution of the tetrahydropyranyl ether from Step 3 (2.8 g, 0.00531 mol) and p-toluene sulfonic acid (1.04 g, 0.00548 mol) in absolute ethanol was stirred (25° C.) for 18 hours. The resulting solution was taken up in dichloromethane (450 ml), washed with saturated $NaHCO_3$ (2×150 ml), washed with brine (1×150 ml), and concentrated under reduced pressure to yield 2.43 g of the title compound as an oil.

$^1$H NMR (90 MHz, $CDCl_3$): δ7.05 (d, 4H), 6.25 (d, 1H), 5.20 (dd, 1H), 4.30 (br s, 2H), 4.10 (q, 2H), 2.30–3.60 (m, 10H), 1.64 (m, 2H), 1.20 (m, 9H).

Step 5: Preparation of [4α,6β(E)]-6-[2-[2,6-diethyl-4-(4-fluorophenyl)-5-hydroxymethyl)-3-pyridinyl]-ethenyl]tetrahydro-4-hydroxy-2H-pyran-2-one The procedures of Steps 9–11 of Example 1 were used to prepare the title compound, mp 161°–164° C.

Analyzed for $C_{23}H_{26}FNO_4$: Calculated: C, 69.16%; H, 6.56; N, 3.51%. Found: C, 68.68%, H, 6.57%; N, 3.32%.

EXAMPLE 37

Preparation of [R*,S*-(E)]-7-[2,6-diethyl-4-(4-fluorophenyl)-5-(hydroxymethyl)-3-pyridinyl]-3,5-dihydroxy-6-heptenoic acid, monosodium salt Using the general method of Example 3, the title compound was prepared, mp 140°–150° C. (dec).

EXAMPLE 38

Preparation of [4α,6β(E)]-6-[2-[4-(4-fluorophenyl)-5-methoxy-6-methyl-2-(1-methylethyl)-3-pyridinyl]ethenyl]tetrahydro-4-hydroxy-2H-pyran-2-one

Step 1: Preparation of 4-(4-Fluorophenyl)-5-formyl-6-methyl-2-(1-methylethyl)-3-pyridinecarboxylic acid, methyl ester The procedures of Steps 1–4 of Example 1 were used to prepare the title compound.

Step 2: Preparation of 4-(4-Fluorophenyl)-5-hydroxy-6-methyl-2-(1-methylethyl)-3-pyridinecarboxylic acid, methyl ester, 1-oxide A solution of 4-(4-fluorophenyl)-5-formyl-6-methyl-2-(1-methylethyl)-3-pyridinecarboxylic acid, methyl ester (1.0 g, 0.00317 mol) and m-chloroperoxybenzoic acid (1.68 g, 65%) in dichloromethane was heated under reflux for 16 hours. The resulting solution was taken up in ethyl acetate (100 ml), washed with saturated $NaHCO_3$ (2×35 ml), washed with brine (1×35 ml), dried ($MgSO_4$), and concentrated under reduced pressure. The resulting oil was dissolved in 10 ml of THF, and 3.8 ml of 1.0N NaOH was added along with enough methanol to render the mixture homogeneous. The resulting solution was stirred one hour (25° C.) then concentrated under reduced pressure. The residue was partitioned between ethyl acetate and water. The water layer was acidified with 1.0N HCl and extracted with ethyl acetate (3×35 ml). The combined organics were washed with brine (1×25 ml), dried ($MgSO_4$), and concentrated under reduced pressure to yield 0.65 g of the title compound as a white powder, mp 240°–243° C. (dec).

Step 3: Preparation of 4-(4-Fluorophenyl)-5-methoxy-6-methyl-2-(1-methylethyl)-3-pyridinecarboxylic acid, methyl ester, 1-oxide A solution of 4-(4-fluorophenyl)-5-hydroxy-6-methyl-2-(1-methylethyl)-3-pyridinecarboxylic acid, methyl ester, 1-oxide (0.65 g, 0.00204 mol), methyl iodide (0.25 ml, 0.00407 mol), and potassium carbonate (0.56 g, 0.00407 mol) in acetone (20 ml) was heated under reflux for two hours followed by concentration of the solvent. The residue was taken up in ethyl acetate (100 ml), washed with brine (2×35 ml), dried ($MgSO_4$), concentrated under reduced pressure, and chromatographed on silica (1:1 hexane:ethyl acetate) to yield 0.50 g of the title compound.

$^1$H NMR (90 MHz, CDCl$_3$): δ6.80–7.30 (m, 4H), 3.50 (s, 3H), 3.30 (overlapping m, 1H, s, 3H), 2.50 (s, 3H), 1.40 (d, 6H).

Step 4: Preparation of 4-(4-Fluorophenyl)-5-methoxy-6-methyl-2-(1-methylethyl)-3-pyridinecarboxylic acid, methyl ester Phosphoroustrichloride (0.55 ml) was added dropwise to a cooled (0° C.) stirring solution of 4-(4-fluorophenyl)-5-methoxy-6-methyl-2-(1-methylethyl)-3-pyridinecarboxylic acid, methyl ester, 1-oxide (0.40 g, 0.002 mmol) in dichloromethane (10 ml). The resulting solution was heated under reflux for one hour, then cooled. Water (ca. 30 ml) and chloroform (25 ml) was added and the mixture was made basic (pH 11) by adding 1.0N NaOH. The layers were separated and the aqueous layer was extracted with chloroform (2×2.5 ml). The combined organics were dried (MgSO$_4$) and concentrated under reduced pressure to yield 0.40 g of the title compound as an oil.

$^1$H NMR (90 MHz, CDCl$_3$): δ6.85–7.30 (m, 4H, 3.49 (s, 3H), 3.26 (s, 3H), 2.90 (m, 1H), 2.50 (s, 3H), 1.27 (d, 6H).

Step 5: Preparation of [4α,6β(E)]-6-[2-[4-(4-fluorophenyl)-5-methoxy-6-methyl-2-(1-methylethyl)-3-pyridinyl]ethenyl]tetrahydro-4-hydroxy-2H-pyran-2-one The procedures of Steps 3–11 of Example 1 were used to prepare the title compound, mp 126°–130° C.

Analyzed for C$_{23}$H$_{26}$FNO$_4$Calculated: C, 69.16%; H, 6.56%; N, 3.51%. Found: C, 69.14%; H, 6.64%; N, 3.26%.

EXAMPLE 39

Preparation of [R*,S*-(E)]-7-[4-(4-fluorophenyl)-5-methoxy-6-methyl-2-(1-methylethyl)-3-pyridinyl]-3,5-dihydroxy-6-heptenoic acid, monosodium salt Using the general method of Exampale 3, the title compound was prepared, mp 210°–225° C. (dec).

EXAMPLE 40

Preparation of [4α,6β(E)]-6-[2-[5-ethenyl-4-(4-fluorophenyl)-6-methyl-2-(1-methylethyl)-3-pyidinyl]ethenyl]tetrahydro-4-hydroxy-2H-pyran-2-one Step 1: Preparation of 5-Ethenyl-4-(4-fluorophenyl)-6-methyl-2-(1-methylethyl)-3-pyridinecarboxylic acid, methyl ester n-Butyllithium (16.0 ml, 2.5M in hexane) was added dropwise with stirring to a cooled (0° C.) slurry of methyltriphenylphosphonium bromide (14.16 g, 0.0396 mol) in dry THF (200 ml). The resulting orange solution was stirred 10 minutes (0° C.), then cooled to −78° C., and a solution of 4-(4-fluorophenyl)-5-formyl-67-methyl-2-(1-methylethyl)-3-pyridinecarboxylic acid, methyl ester (10.0 g, 0.0317 mol, prepared in Example 38) in dry THF (60 ml) was added dropwise. The resulting solution was allowed to warm to room temperature and was stirred 16 hours followed by concentration of the solvent. The residue was taken up in dichloromethane (450 ml), washed with brine (1×150 ml), dried (MgSO$_4$), concentrated under reduced pressure, and chromatographed on silica (90:10 hexane:ethyl acetate) to yield 9.65 g of the title compound as an oil.

$^1$H NMR (90 MHz, CDCl$_3$): δ 7.05 (m, 4H), 6.28 (dd, 1H), 5.20 (dd, 1H), 4.95 (dd, 1H), 3.43 (s, 3H), 2.94 (m, 1H), 2.56 (s, 3H), 1.25 (d, 6H).

Step 2: Preparation of [4α,6β(E)]-6-[2-[5-Ethenyl-4-(4-fluorophenyl)-6-methyl-2-(1-methylethyl)-3-pyridinyl]ethenyl]-tetrahydro-4-hydroxy-2H-pyran-2-one The procedures of Steps 3–11 of Example 1 were used to prepare the title compound, mp 148°–149.5° C.

Analyzed for C$_{24}$H$_{26}$FNO$_3$: Calculated: C, 72.89%; H, 6.63%; N, 3.54%. Found: C, 72.80%; H, 6.69%; N, 3.32%.

EXAMPLE 41

Preparation of [R*,S*-(E)]-7-[5-ethenyl-4-(4-fluorophenyl)-6-methyl-2-(1-methylethyl)-3-pyridinyl]-3,5-dihydroxy-6-heptenoic acid, monosodium salt Using the general method of Example 3, the title compound was prepared, mp 185°–195° C. (dec).

EXAMPLE 42

Preparation of 4α,6β(E)-6-[2-[4-(4-fluorophenyl)-6-methyl-2-(1-methylethyl)-3-pyridinyl]ethenyl]tetrahydro-4-hydroxy-2H-pyran-2-one, N-oxide Using the general method of Example 17, the title compound was prepared, mp 188°–191° C.

Analyzed for C$_{22}$H$_{24}$FNO$_4$: Calculated: C, 68.56%; H, 6.28%; N, 3.63%. Found: C, 68.26%; H, 6.15%; N, 3.41%.

EXAMPLE 43

[R*,S*-(E)]-7-[4-(4-fluorophenyl)-6-methyl-2-(1-methylethyl)-3-pyridinyl]-3,5-dihydroxy-6-heptenoic acid, N-oxide, monosodium salt Using the general method of Example 3, the title compound was prepared, mp 120°–130° C.

Analyzed for C$_{22}$H$_{25}$FNO$_5$Na: Calculated: C, 59.59%; H, 5.68%; N, 3.16%. Found: C, 58.90%; H, 6.18%; N, 2.83%.

EXAMPLE 44

[4α,6β(E)]-6-[2-[2,6-diethyl-4-(4-fluorophenyl)]-3-pyridinyl]ethenyl]tetrahydro-4-hydroxy-2H-pyran-2-one, N-oxide Using the general method of Example 17, the title compound was prepared, mp 188°–191° C.

We claim:

1. A compound of structural Formula I

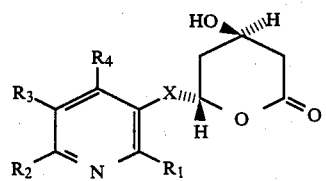

and the N-oxide thereof, wherein
X is —CH2CH2— or —CH=CH—;
R$_1$ and R$_4$ are each independently
  alkyl of from one to six carbons;

trifluoromethyl;
cyclopropyl;
cyclohexyl;
cyclohexylmethyl;
phenyl;
phenyl substituted with
   fluorine,
   chlorine,
   bromine;
   hydroxy,
   trifluoromethyl,
   alkyl of from one to four carbon atoms, or
   alkoxy of from one to four carbon atoms;
phenylmethyl;
phenylmethyl substituted with
   fluorine,
   chlorine,
   bromine;
   hydroxy,
   trifluoromethyl,
   alkyl of from one to four carbon atoms, or
   alkoxy of from one to four carbon atoms;
2-pyridinyl;
2-pyridinyl-N-oxide;
3-pyridinyl;
3-pyridinyl-N-oxide;
4-pyridinyl;
4-pyridinyl-N-oxide;
2-pyrimidinyl;
4-pyrimidinyl;
5-pyrimidinyl;
2-thienyl;
3-thienyl;
$CH_2OH$;
chlorine;
bromine;
NR'R" wherein R' and R" are each independently hydrogen, alkyl of from one to four carbon atoms, or together with the N to which they are attached form

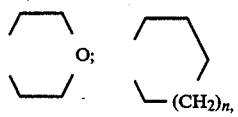

wherein n' is an integer of from 0 to 5;

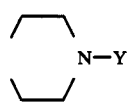

wherein Y is hydrogen or an alkyl of from one to four carbon atoms;
or $R_1$ is
   CN;
   OR; or
   $S(O)_nR$
   wherein n is 0, 1, or 2 and R is lower alkyl phenyl, substituted phenyl, benzyl or substituted benzyl;
$R_2$ is
   hydrogen;
   alkyl of from one to six carbon atoms;
   trifluoromethyl;
   cyclopropyl;
   phenyl;
   phenyl substituted with
      fluorine,
      chlorine,
      bromine;
      hydroxy,
      trifluoromethyl,
      alkyl of from one to four carbon atoms, or
      alkoxy of from one to four carbon atoms;
   2-pyridinyl;
   2-pyridinyl-N-oxide;
   3-pyridinyl;
   4-pyridinyl;
   2-pyrimidinyl;
   4-pyrimidinyl;
   5-pyrimidinyl;
   2-thienyl;
   3-thienyl;
   $CH_2OH$;
   chlorine;
   bromine; or
   NR'R" wherein R' and R" are as above;
$R_3$ is
   hydrogen;
   alkyl of from one to six carbon atoms;
   cyano;
   nitro;
   $-NR_5R_6$ where $R_5$ and $R_6$ are independently hydrogen or alkyl of from one to four carbon atoms;
   phenyl;
   $-NHCOR_7$ where $R_7$ is alkyl of from one to four carbon atoms;
   $-COR_8$ where $R_8$ is
      hydroxyl,
      alkoxyl of from one to six carbon atoms,
      phenoxy,
      $NR_5R_6$, where $R_5$ and $R_6$ are as defined above,
      vinyl,
      alkoxy of from one to four carbon atoms,
      hydrogen, or
      $CH_2OH$;
a corresponding dihydroxy-acid compound of Formula II corresponding to the opened form of the lactone ring of a compound of Formula I above

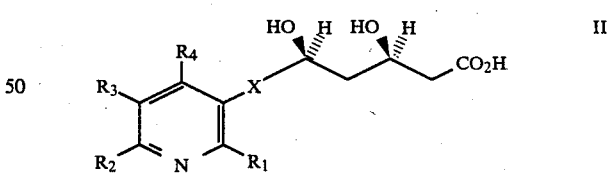

or the N-oxide thereof, wherein X, $R_1$, $R_2$, $R_3$, and $R_4$ are as defined above, or a lower alkyl ester or pharmaceutically acceptable salt thereof, all of the compounds being in the trans racemate of the tetrahydropyran moiety.

2. A compound as defined by claim 1 having structural Formula I.

3. A compound as defined by claim 1 wherein X is —CH=CH—.

4. A compound as defined by claim 1 wherein X is —$CH_2CH_2$—.

5. A compound as defined by claim 2 having the name trans-tetrahydro-4-hydroxy-6-[2-(2-methyl-4-phenyl-3-pyridinyl)ethyl]-2H-pyran-2-one.

6. A compound as defined by claim 2 having the name [4α,6β(E)]-tetrahydro-4-hydroxy-6-[2-(2-methyl-4-phenyl-3-pyridinyl)ethenyl]-2H-pyran-2-one.

7. A compound as defined by claim 2 having the name [4α,6β(E)]-6-[2-(2,6-dimethyl-4-phenyl-3-pyridinyl)ethenyl]tetrahydro-4-hydroxy-2H-pyran-2-one.

8. A compound as defined by claim 2 having the name [4α,6β(E)]-6-[2-[4-(4-fluorophenyl)-2,6-dimethyl-3-pyridinyl]ethenyl]tetrahydro-4-hydroxy-2H-pyran-2-one.

9. A compound as defined by claim 1 having the name [2α,4β(E)]-4-(4-fluorophenyl)-2,6-dimethyl-5-[2-(tetrahydro-4-hydroxy-6-oxo-2H-pyran-2-yl)ethenyl]-3-pyridinecarbonitrile.

10. A compound as defined by claim 1 selected from the group consisting of

[4α,6β(E)]-6-[2-(4-fluorophenyl)-2,6-bis(1-methylethyl)-3-pyridinyl]ethenyl]tetrahydro-4-hydroxy-2H-pyran-;b 2-one;

[R*,S*(E)]-7-[4-(4-fluorophenyl)-2,6-bis(1-methylethyl)-3-pyridinyl]-3,5-dihydroxy-6-heptenoic acid, monosodium salt;

[4α,6β(E)]-6-[2-[4-(4-fluorophenyl)-6-methyl-2-(1-methylethyl)-3-pyridinyl]ethenyl]tetrahydro-4-hydroxy-2H-pyran-2-one;

[R*,S*-(E)]-7-[4-(4-fluorophenyl)-6-methyl-2-(1-methylethyl)-3-pyridinyl]-3,5-dihydroxy-6-heptenoic acid, monosodium salt;

[R*,S*-(E)]-7-[4-(4-fluorophenyl)-6-methyl-2-(1-methylethyl)-3-pyridinyl]-3,5-dihydroxy-6-heptenoic acid, hemicalcium salt;

[4α,6β(E)]-6-[2-[2,6-diethyl-4-(4-fluorophenyl)-3-pyridinyl]ethenyl]tetrahydro-4-hydroxy-2H-pyran-2-one;

[R*,S*-(E)]-7-[2,6-diethyl-4-(4-fluorophenyl)-3-pyridinyl]-3,5-dihydroxy-6-heptenoic acid, monosodium salt;

[4α,6β(E)]-6-[2-[4-(4-fluorophenyl)-5-methoxy-6-methyl-2-(1-methylethyl)-3-pyridinyl]ethenyl]tetrahydro-4-hydroxy-2H-pyran-2-one;

[R*,S*-(E)]-7-[4-(4-fluorophenyl)-5-methoxy-6-methyl-2-(1-methylethyl)-3-pyridinyl]-3,5-dihydroxy-6-heptenoic acid, monosodium salt;

[4α,6β(E)]-6-[2-[5-ethenyl-4-(4-fluorophenyl)-6-methyl-2-(1-methylethyl)-3-pyridinyl]ethenyl]tetrahydro-4-hydroxy-2H-pyran-2-one;

[R*,S*-(E)]-7-[5-ethenyl-4-(4-fluorophenyl)-6-methyl-2-(1-methylethyl)-3-pyridinyl]-3,5-dihydroxy-6-heptenoic acid, monosodium salt;

[4α,6β(E)]-6-[2-[4-(4-fluorophenyl)-6-methyl-2-(1-methylethyl)-3-pyridinyl]ethenyl]tetrahydro-4-hydroxy-2H-pyran-2-one, N-oxide;

[R*,S*-(E)]-7-(4-(4-fluorophenyl)-6-methyl-2-(1-methylethyl)-3-pyridinyl]-3,5-dihydroxy-6-heptenoic acid, N-oxide, monosodium salt.

11. A pharmaceutical composition for inhibiting cholesterol biosynthesis comprising an effective amount of a compound as defined by claim 1 in combination with a pharmaceutically acceptable carrier.

12. A method of inhibiting cholesterol biosynthesis in a patient in need of said treatment comprising administering a cholesterol synthesis inhibiting amount of a compound as defined by claim 1 in combination with a pharmaceutically acceptable carrier.

* * * * *

UNITED STATES PATENT AND TRADEMARK OFFICE
CERTIFICATE OF CORRECTION

PATENT NO. : 4,906,624

DATED : March 6, 1990

INVENTOR(S) : Alexander W. Chucholowski, et al

It is certified that error appears in the above-identified patent and that said Letters Patent is hereby corrected as shown below:

Column 32, lines 43 to 59 should be deleted.

Signed and Sealed this

Twenty-ninth Day of October, 1991

*Attest:*

HARRY F. MANBECK, JR.

*Attesting Officer*         *Commissioner of Patents and Trademarks*